US008420230B2

(12) United States Patent
Yang et al.

(10) Patent No.: US 8,420,230 B2
(45) Date of Patent: Apr. 16, 2013

(54) ORGANIC LIGHT EMITTING DIODE EMPLOYING LUMINESCENT EFFICIENCY IMPROVEMENT LAYER

(75) Inventors: Seung-Gak Yang, Yongin (KR); Hee-Yeon Kim, Yongin (KR); Jae-Yong Lee, Yongin (KR); Jong-Hyuk Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 114 days.

(21) Appl. No.: 12/461,547

(22) Filed: Aug. 14, 2009

(65) Prior Publication Data

US 2010/0039026 A1  Feb. 18, 2010

(30) Foreign Application Priority Data

Aug. 18, 2008 (KR) .................. 10-2008-0080568

(51) Int. Cl.
*H01L 51/50* (2006.01)
(52) U.S. Cl.
USPC ........... 428/690; 428/917; 313/504; 313/505; 313/506; 546/18; 546/24; 544/234
(58) Field of Classification Search .......... 428/690, 428/917; 313/112, 504, 505, 506, 113; 257/98, 257/40; 546/18, 24; 544/234
See application file for complete search history.

(56) References Cited

U.S. PATENT DOCUMENTS

| | | | | |
|---|---|---|---|---|
| 6,057,048 A | * | 5/2000 | Hu et al. ............. | 428/690 |
| 6,225,467 B1 | * | 5/2001 | Esteghamatian et al. ..... | 544/180 |
| 2005/0062407 A1 | * | 3/2005 | Suh et al. ................ | 313/504 |
| 2007/0051944 A1 | | 3/2007 | Vestweber et al. | |
| 2008/0023724 A1 | | 1/2008 | Takeda et al. | |

FOREIGN PATENT DOCUMENTS

| | | | |
|---|---|---|---|
| JP | 2002-212170 | * | 7/2002 |
| JP | 2003045662 | | 2/2003 |
| JP | 2006004721 | | 1/2006 |
| JP | 2006302878 | | 11/2006 |
| KR | 20030029467 | | 4/2003 |
| KR | 20040080474 | | 9/2004 |
| KR | 20070009074 | | 1/2007 |

OTHER PUBLICATIONS

Korean Registration Determination Certificate issued by Korean Patent Office on Apr. 20, 2010 corresponding Korean Patent Application No. 10-2008-0080568 and Request for Entry of the Accompanying Documents attached herewith.

(Continued)

*Primary Examiner* — Jennifer A Chriss
*Assistant Examiner* — Gregory Clark
(74) *Attorney, Agent, or Firm* — Robert E. Bushnell, Esq.

(57) ABSTRACT

Provided is an organic light emitting diode employing a luminescent efficiency improvement layer containing a compound represented by Formula 1 below:

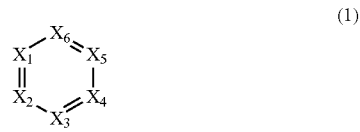

(1)

The OLED including the luminescent efficiency improvement layer containing the compound represented by Formula 1 can have excellent luminescent efficiency.

22 Claims, 1 Drawing Sheet

OTHER PUBLICATIONS

Su et al., Pyridine-Containing Bipolar Host Materials for Highly Efficient Blue Phosphorescent OLEDs, Chemistry of Materials, 2008, 20, p. 1691-1693. Cited in attached Taiwanese Office Action issued by Taiwanese Patent Office on Oct. 22, 2012 in connection with Taiwanese Patent Application Serial No. 098127566 which also claims Korean Patent Application Serial No. 10-2008-0080568 as its priority document.
Taiwanese Office Action issued by Taiwanese Patent Office on Oct. 22, 2012 in connection with Taiwanese Patent Application Serial No. 098127566 which also claims Korean Patent Application Serial No. 10-2008-0080568 as its priority document and Request for Entry of the Accompanying Office Action attached herewith.
Japanese Office Action issued on May 29, 2012 by JPO in connection with Japanese Patent Application No. 2009-189375, which also claims to Korean Patent Application No. 2008-0080568 as its priority document and Request for Entry of the Accompanying Office Action attached herewith.

* cited by examiner

ORGANIC LIGHT EMITTING DIODE EMPLOYING LUMINESCENT EFFICIENCY IMPROVEMENT LAYER

CROSS-REFERENCE TO RELATED PATENT APPLICATION

This application claims the benefit of Korean Patent Application No. 10-2008-0080568, filed on Aug. 18, 2008, in the Korean Intellectual Property Office, the disclosure of which is incorporated herein in its entirety by reference.

BACKGROUND OF THE INVENTION

1. Field of the Invention

The present invention relates to an organic light emitting diode (OLED). employing a luminescent efficiency improvement layer.

2. Description of the Related Art

Organic light emitting diodes (OLEDs), which are self-emitting devices, have advantages such as a wide viewing angle, excellent contrast, quick response, high brightness, excellent driving voltage characteristics, and can provide multicolored images.

A typical OLED has a structure including a substrate, and an anode, a hole transport layer (HTL), an emissive layer (EML), an electron transport layer (ETL), and a cathode which are sequentially stacked on the substrate. In this regard, the HTL, the EML, and the ETL are generally organic thin films formed of organic compounds.

A principle of operation of the OLED having the above-described structure is as follows.

When a voltage is applied to the anode and the cathode, holes injected from the anode move to the EML via the HTL, and electrons injected from the cathode move to the EML via the ETL. The holes and electrons recombine in the EML to generate excitons. When the energy state of the excitons drop from an excited state to a ground state, light is emitted.

Luminescent efficiency of an OLED may be categorized into internal luminescent efficiency and external luminescent efficiency. Internal luminescent efficiency is influenced by how efficiently excitons are generated and converted into light in organic layers such as HTL, EML, and ETL which are interposed between a first electrode and a second electrode (i.e., between an anode and a cathode). On the other hand, external luminescent efficiency (light coupling efficiency) is influenced by how efficiently light generated in the organic layers is extracted out of the OLED. The luminescent efficiency of the OLED is reduced if the external luminescent efficiency is low, even if the luminescent efficiency in the organic layers is high (i.e., internal liminescnet efficiency is high).

SUMMARY OF THE INVENTION

The present Invention an improved organic light emitting diode (OLED).

According to an aspect of the present invention, there is provided an organic light emitting diode (OLED) including: a substrate; a first electrode formed on the substrate, the first electrode having a second surface facing the substrate and a first surface opposite to the substrate; an organic layer formed on the first electrode, the organic layer facing the first surface of the first electrode; a second electrode formed on the organic layer, the second electrode having a first surface facing the organic layer and a second surface opposite to the organic layer; and a luminescent efficiency improvement layer formed on at least one of the second surface of the second electrode and the second surface of the first electrode, the luminescent efficiency improvement layer including a compound represented by Formula 1 below:

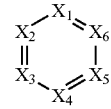

Formula 1 wherein $X_1$ is N or a group represented by $C\text{—}(Ar_1)_a\text{—}R_1$;
$X_2$ is N or a group represented by $C\text{—}(Ar_2)_b\text{—}R_2$;
$X_3$ is N or a group represented by $C\text{—}(Ar_3)_c\text{—}R_3$;
$X_4$ is N or a group represented by $C\text{—}(Ar_4)_d\text{—}R_4$;
$X_5$ is N or a group represented by $C\text{—}(Ar_5)_e\text{—}R_5$;
$X_6$ is N or a group represented by $C\text{—}(Ar_6)_f\text{—}R_6$, with the proviso that at east one of $X_1$ to $X_6$ is N;
$Ar_1$ to $Ar_6$ are each independently a substituted or unsubstituted $C_6\text{-}C_{30}$ arylene group or a substituted or unsubstituted $C_2\text{-}C_{30}$ heteroarylene group;
$R_1$ to $R_6$ are each independently a hydrogen atom, a halogen atom, a hydroxyl group, a cyano group, a substituted or unsubstituted $C_1\text{-}C_{30}$ alkyl group, a substituted or unsubstituted $C_1\text{-}C_{30}$ alkoxy group, a substituted or unsubstituted $C_1\text{-}C_{30}$ acyl group, a substituted or unsubstituted $C_2\text{-}C_{30}$ alkenyl group, a substituted or unsubstituted $C_2\text{-}C_{30}$ alkynyl group, a substituted or unsubstituted $C_6\text{-}C_{30}$ aryl group, or a substituted or unsubstituted $C_2\text{-}C_{30}$ heteroaryl group, wherein at least two adjacent groups of $R_1$ to $R_6$ may be optionally bonded to each other to form a saturated or unsaturated ring; and
a, b, c, d, e and f are each independently an integer of 0 to 10.

According to an aspect of the present invention, there is provided an organic light emitting diode (OLED) including: a substrate; a first electrode formed on the substrate, a second electrode having a first surface facing the first electrode and a second surface opposite to the first surface; an organic layer interposed between the first electrode and the second electrode; a first luminescent efficiency improvement layer formed on the second surface of the electrode, the first luminescent efficiency improvement layer comprising a compound represented by the above Formula 1.

According to an aspect of the present invention, there is provided an organic light emitting diode (OLED) including: a substrate; a first electrode formed on the substrate; a second electrode having a first surface facing the first electrode and a second surface opposite to the first surface; an organic layer interposed between the first electrode and the second electrode; a luminescent efficiency improvement layer formed between the substrate and the first electrode, the luminescent efficiency improvement layer comprising a compound represented by the above Formula 1.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Hereinafter, the present invention will be described more fully with reference to the companying drawings, in which exemplary embodiments of the invention are shown.

Figure 1:
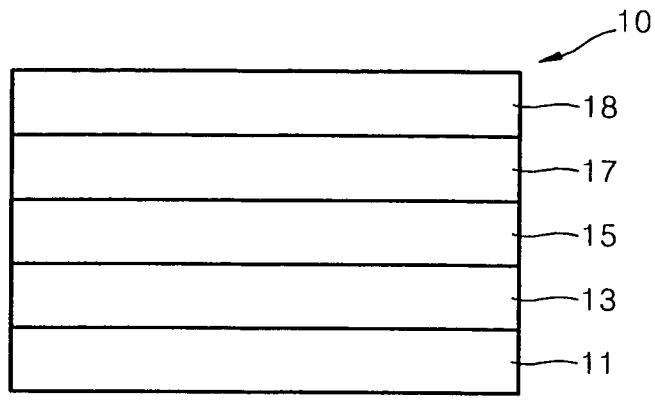
FIG. 1 is a schematic sectional view of an organic light emitting diode (OLED) according to an embodiment of the present invention.

FIG. 1 is a schematic sectional view of an organic light emitting diode (OLED) 10 according to an embodiment of the present invention.

Referring to FIG. 1, the OLED 10 according to the present embodiment includes a substrate 11, a first electrode 13, an organic layer 15, a second electrode 17, and a luminescent efficiency improvement layer 18 which are sequentially stacked in this order. The second electrode 17 may be a transmission electrode, and light generated in the organic layer 15 passes through the second electrode 17 and the luminescent efficiency improvement layer 18 before being transmitted out of the OLED 10.

The substrate 11 may be any substrate that is used in conventional organic light emitting devices. For example, the substrate 11 may be a glass substrate or a transparent plastic substrate with excellent mechanical strength, thermal stability, transparency, surface smoothness, ease of handling, and waterproofness.

The first electrode 13 may be formed by depositing or sputtering a material on the substrate. The first electrode 13 has a first surface contacting with the organic layer 15 and a second surface being opposite to the organic layer 15. If the first electrode 13 is an anode, the material used to form the first electrode 13 may be a high work-function material so as to facilitate hole injection. The first electrode 13 may be a reflective electrode or a transmission electrode. Transparent and conductive materials such as indium tin oxide (ITO), indium zinc oxide (IZO), $SnO_2$, and ZnO may be used to form the first electrode 13. When the first electrode 13 is a reflective electrode, the first electrode 13 may be formed using Mg, Al, Al—Li, Ca, Mg—In, Mg—Ag, or the like.

The organic layer 15 may be formed on the first electrode 13. The term "organic layer" used herein indicates any layer interposed between the first electrode 13 and the second electrode 17. The organic layer 15 is not limited to an organic layer formed of pure organic materials. For example, the organic layer may include a metal complex.

The organic layer 15 may include at least one of a hole injection layer (HIL), a hole transport layer (HTL), an emissive layer (EML), a hole blocking layer (HBL), an electron transport layer (ETL) and an electron injection layer (EIL).

The HIL may be formed on the first electrode 13 by vacuum deposition, spin coating, casting, Langmuir-Blodgett (LB) deposition, or the like.

When the HIL is formed using vacuum deposition, the deposition conditions may vary according to a compound that is used to form the HIL, and the structure and thermal properties of the HIL to be formed. In general, however, conditions for vacuum deposition may include a deposition temperature of 100 to 500° C., a pressure of $10^{-8}$ to $10^{-3}$ torr, and a deposition rate of 0.01 to 100 Å/sec.

When the HIL is formed using spin coating, the coating conditions may vary according to a compound that is used to form the HIL, and the structure and thermal properties of the HIL to be formed. In general, the coating rate may be in the range of 2,000 to 5,000 rpm, and a temperature for heat treatment which is performed to remove a solvent after coating may be in the range of 80 to 200° C.

The HIL may be formed of any material that is commonly used to form a HIL. Examples of the material that can be used to form the HIL are a phthalocyanine compound such as copperphthalocyanine, 4,4',4''-tris(3-methylphenylphenylamino)triphenylamine (m-MTDATA), N,N'-di(1-naphthyl)-N,N'-diphenylbenzidine (NPB), 4,4',4''-tris(N,N-diphenylamino)-triphenylamine (TDATA), 4,4',4''-tris[2-naphthyl(phenyl)amino]triphenylamine (2TNATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline)/poly(4-styrenesulfonate (PANI/PSS), but are not limited thereto.

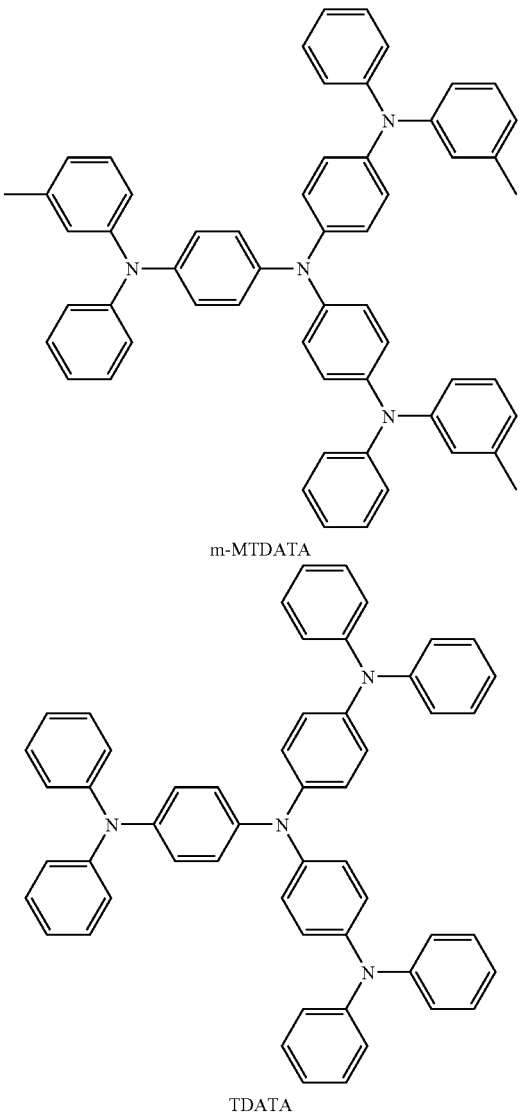

m-MTDATA

TDATA

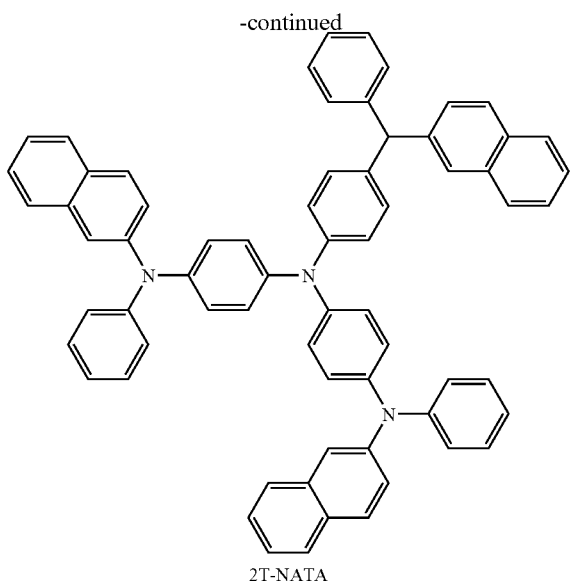

2T-NATA

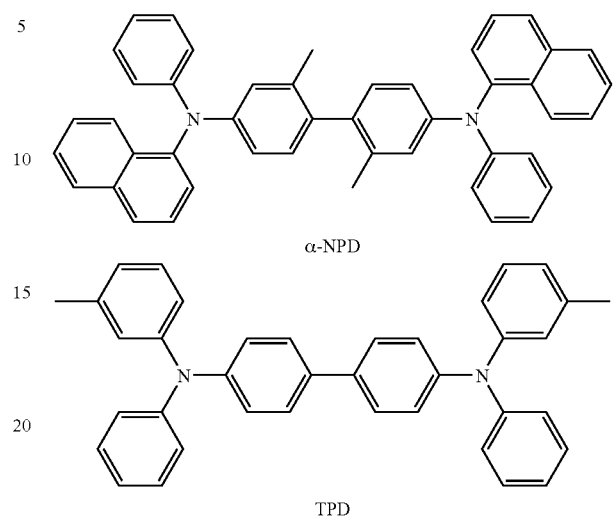

α-NPD

TPD

The thickness of the HIL may be in the range of about 100 Å to 10,000 Å, and preferably, 100 Å to 1,000 Å. If the thickness of the HIL is within the range described above, an excellent hole injecting ability of the HIL may be obtained without a substantial increase in driving voltage Then a HTL may be formed on the HIL by vacuum deposition, spin coating, casting, LB, or the like. When the HTL is formed by vacuum deposition or spin coating, the conditions for deposition and coating may be similar to those for the formation of the HIL, although the conditions for the deposition and coating may vary according to the material that is used to form the HTL.

The HTL may be formed of any material that is commonly used to form a HTL without limitations. Examples of the material that can be used to form the HTL are: a carbazole derivative such as N-phenylcarbazole and polyvinylcarbazole; an amine derivative having an aromatic condensation ring such as N,N'-bis(3-methylphenyl)-N,N'-diphenyl-[1,1-biphenyl]-4,4'-diamine (TPD), and N,N'-di(naphthalene-1-yl)-N,N'-diphenyl benzydine (α-NPD); and a triphenylamine-based material such as 4,4',4"-tris(N-carbazolyl) triphenylamine (TCTA). Among these materials, TCTA may not only transport holes but also inhibit excitons from being diffused into the emissive layer (EML).

The thickness of the HTL may be in the range of about 50 Å to 1,000 Å, and preferably, 100 Å to 800 Å. If the thickness of the HTL is within the range described above, an excellent hole transporting ability of the HTL may be obtained without a substantial increase in driving voltage.

Then, an EML may be formed on the HTL by vacuum deposition, spin coating, casting, LB, or the like. When the EML is formed by vacuum deposition or spin coating, the conditions for deposition and coating may be similar to those for the formation of the HIL, although the conditions for deposition and coating may vary according to the material that is used to form the EML.

The EML may be formed of a compound, or a combination of a host and a dopant. Example of the host are tri-8-quinolinolatoaluminum (Alq$_3$), 4,4'-N,N'-dicarbazole-biphenyl (CBP), poly(n-vinylcarbazole) (PVK), 9,10-di(naphthalene-2-yl)anthracene (ADN), 4,4',4"-tris(N-carbazolyl)-triphenylamine (TCTA), 1,3,5-tris(N-phenylbenzimidazole-2-yl) benzene (TPBI), 3-tert-butyl-9,10-di-2-naphthylanthracene (TBADN), E3, and distyrylarylene (DSA), but are not limited thereto.

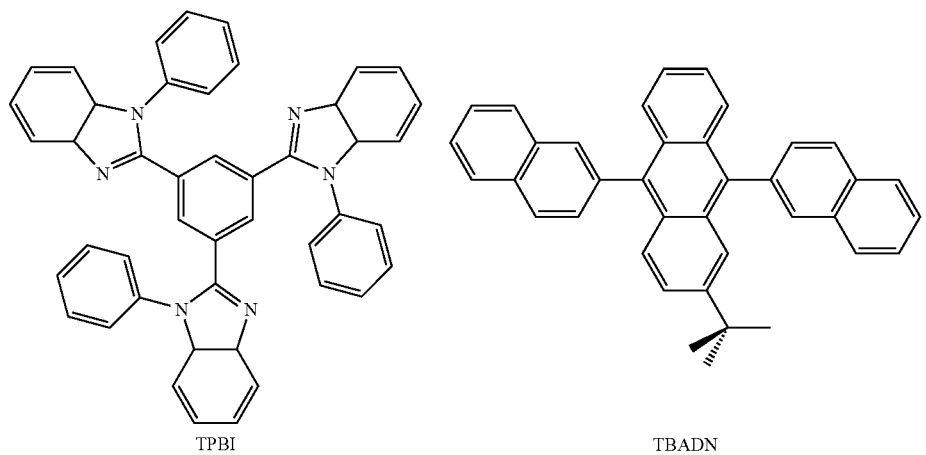

TPBI

TBADN

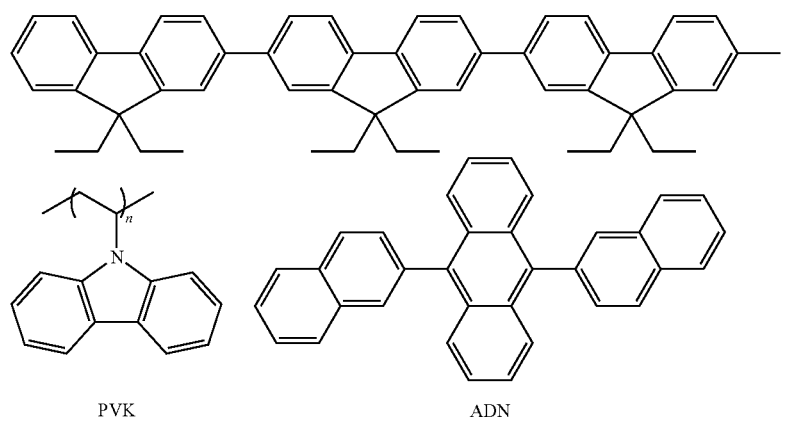

PVK  ADN

A known red dopant may be platinum(II) octaethylporphyrin (PtOEP), Ir(piq)$_3$, Btp$_2$Ir(acac), 4-(dicyanomethylene)-2-tert-butyl-6-(1,1,7,7-tetramethyljulolidin-4-yl-vinyl)-4H-pyran (DCJTB), or the like, but is not limited thereto.

In addition, a known green dopant may be Ir(ppy)$_3$ (ppy=phenylpyridine), Ir(ppy)$_2$(acac), Ir(mpyp)$_3$, 10-(2-Benzothiazolyl)-2,3,6,7-tetrahydro-1,1,7,7-tetramethyl-1H,5H,11H-(1)-benzopyropyrano(6,7-8-i,j)quinolizin-11-one (C545T), or the like, but is not limited thereto.

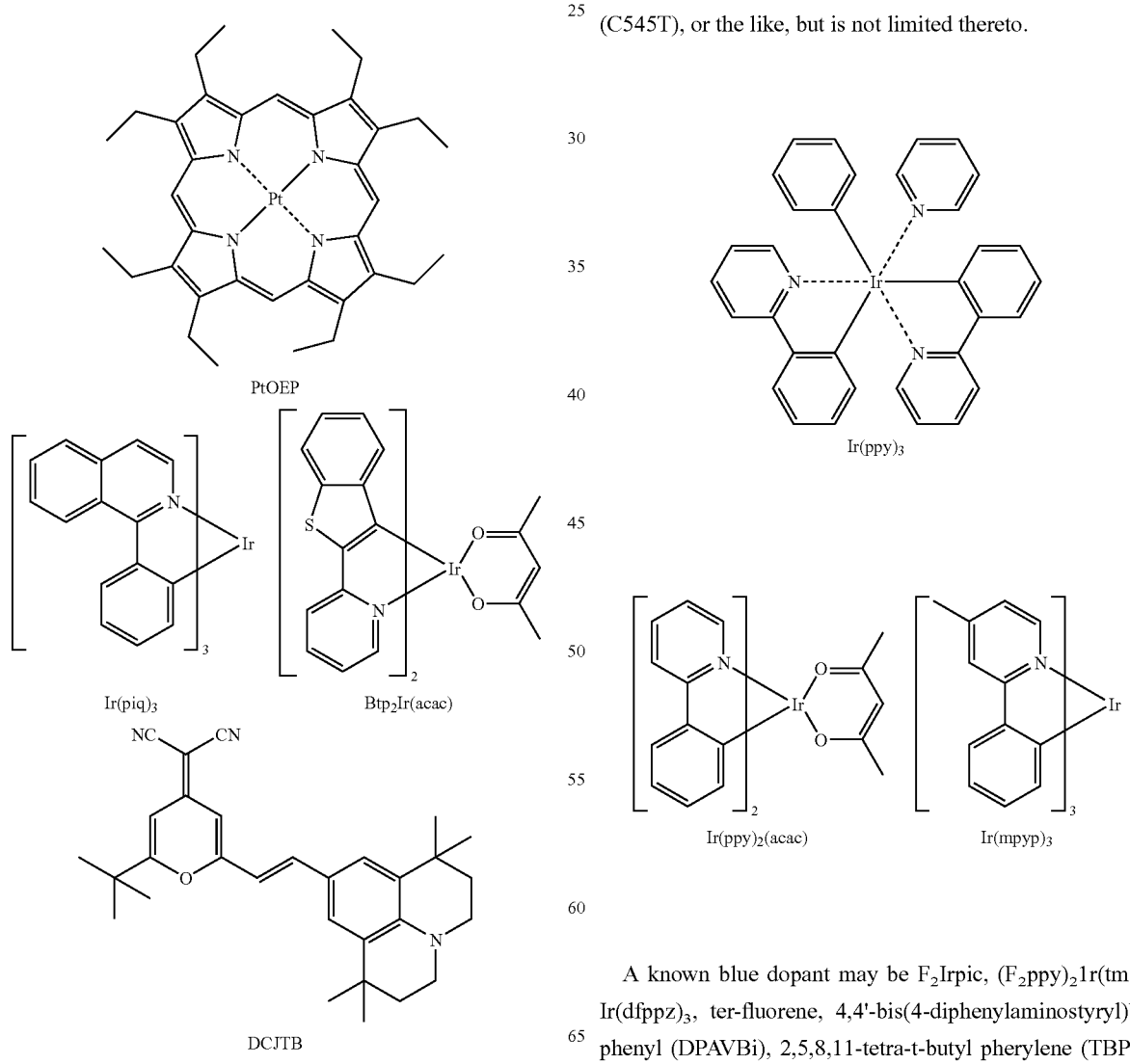

PtOEP

Ir(piq)$_3$  Btp$_2$Ir(acac)

DCJTB

Ir(ppy)$_3$

Ir(ppy)$_2$(acac)  Ir(mpyp)$_3$

A known blue dopant may be F$_2$Irpic, (F$_2$ppy)$_2$Ir(tmd), Ir(dfppz)$_3$, ter-fluorene, 4,4'-bis(4-diphenylaminostyryl)biphenyl (DPAVBi), 2,5,8,11-tetra-t-butyl pherylene (TBPe), or the like, but is not limited thereto.

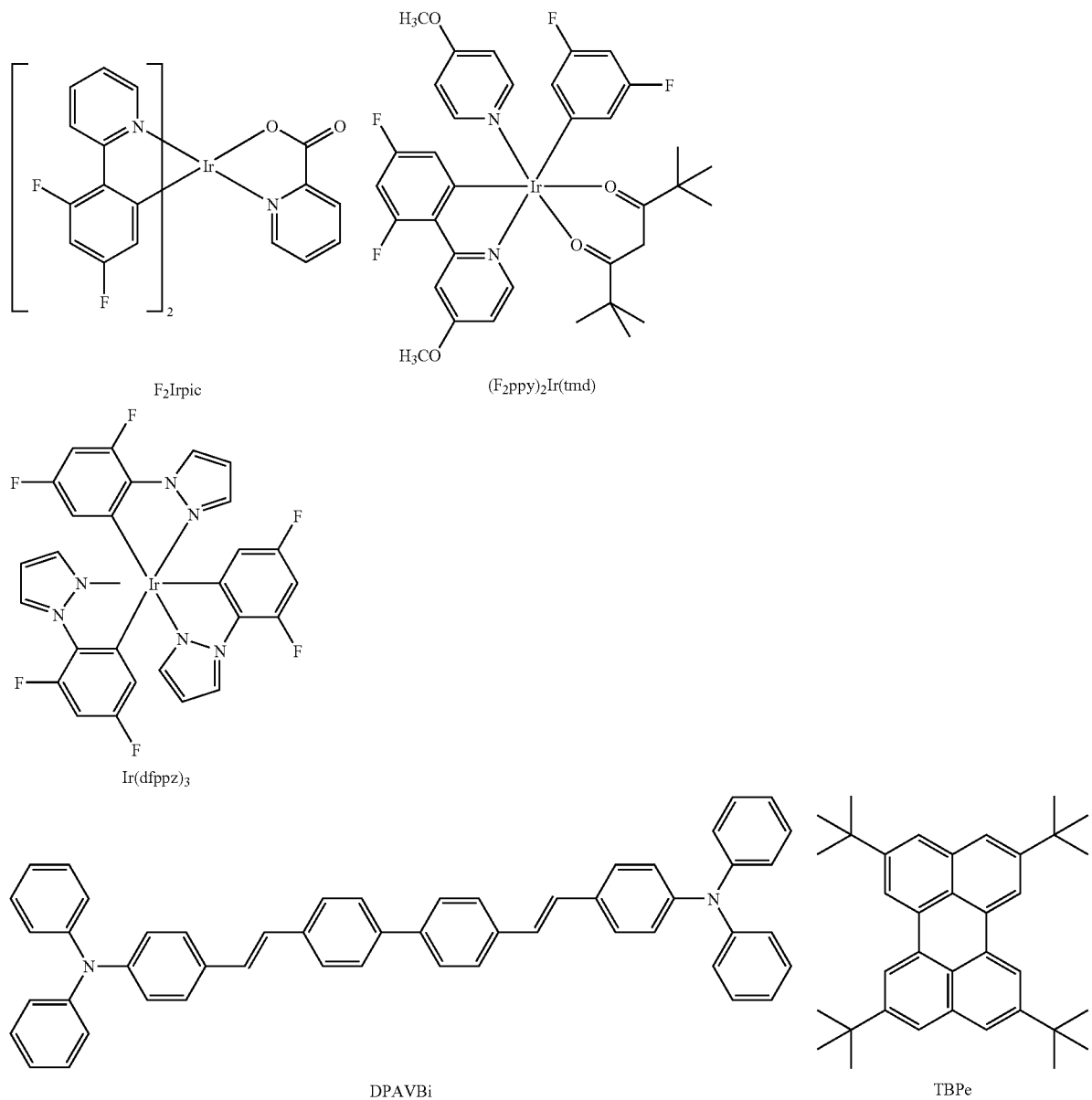

F₂Irpic (F₂ppy)₂Ir(tmd)

Ir(dfppz)₃

DPAVBi

TBPe

If the dopant and the host are used together, the amount of the dopant may be in the range of 0.01 to 15 parts by weight based on 100 parts by weight of the host, but is not limited thereto.

The thickness of the EML may be in the range of about 100 to 1,000 Å, and preferably in the range of 200 to 600 Å. If the thickness of the EML is within the range described above, an excellent emitting ability of the EML may be obtained without a substantial increase in driving voltage.

A HBL may be formed between the ETL and the EML to prevent diffusion of triplet excitons or holes into the ETL when the EML includes a phosphorescent dopant. The HBL may be formed by vacuum deposition, spin coating, casting, LB, or the like. When the HBL is formed by vacuum deposition or spin coating, the conditions for deposition and coating may be similar to those for the formation of the HIL, although the conditions for deposition and coating may vary according to the material that is used to form the HBL. Any material that is commonly used to form a HBL may be used, for example, an oxadiazole derivative, a triazole derivative, or a phenanthroline derivative may be used.

The thickness of the HBL may be in the range of about 50 to 1,000 Å, and preferably 100 to 300 Å. When the thickness of the HBL is within the range described above, an excellent hole blocking ability of the HBL may be obtained without a substantial reduction in driving voltage.

Then an ETL may be formed on the HBL or EML by vacuum deposition, spin coating, casting, or the like. When the ETL is formed by vacuum deposition or spin coating, the deposition and coating conditions may be similar to those for formation of the HIL, although the deposition and coating conditions may vary according to a compound that is used to form the ETL. A material that is used to form the ETL may be a material that can stably transport electrons injected from the electron injecting electrode (cathode) and any known material may be used. For example, the material that is used to form the form the ETL may be a quinoline derivative, in particular, tris(8-quinolinorate)aluminum ($Alq_3$), TAZ, Balq, or the like, which is known in the art, but is not limited thereto.

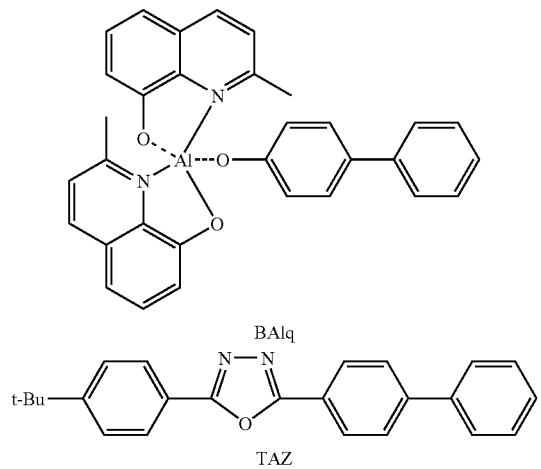

The thickness of the ETL may be in the range of about 100 to 1,000 Å, and preferably in the range of 150 to 500 Å. When the thickness of the ETL is within the range described above, an excellent electron transporting ability of the ETL may be obtained without a substantial increase in driving voltage.

Then an EIL may be formed on the ETL. The EIL may be formed of a material allowing easy injection of electrons from a cathode without limitation.

The material that is used to form the EIL may be LiF, NaCl, CsF, $Li_2O$, BaO, or the like, which is known in the art. Deposition and coating conditions are similar to those for formation of the HIL, although the deposition and coating conditions may vary according to a material that is used to form the EIL.

The thickness of the EIL may be in the range of about 1 to 100 Å, and preferably in the range of 5 to 90 Å. When the thickness of the EIL is within the range described above, an excellent electron injection ability of the EIL may be obtained without a substantial increase in driving voltage.

The second electrode 17, which may be a transmission electrode, is formed on the organic layer 15. The second electrode 17 has a first surface contacting with the organic layer 15 (for example, EIL) and a second surface being opposite to the organic layer 15. The second electrode 17 may be a cathode, which is an electron injecting electrode. A metal that is used to form the second electrode 17 may be a low work-function metal, alloy, an electrically conductive compound, or a combination thereof. In detail, a transmission electrode may be formed using a thin film of Li, Mg, Al, Al—Li, Ca, Mg—In, Mg—Ag, or the like. In addition, the transmission electrode may be formed of ITO or IZO to produce a top emission type light emitting device.

The luminescent efficiency improvement layer 18 is formed on the second surface of the second electrode 17.

The luminescent efficiency improvement layer 18 includes a compound represented by Formula 1 below:

Formula 1

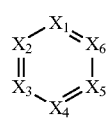

In Formula 1, $X_1$ is N or a group represented by C—$(Ar_1)_a$—$R_1$; $X_2$ is N or a group represented by C—$(Ar_2)_b$—$R_2$; $X_3$ is N or a group represented by C—$(Ar_3)_c$—$R_3$; $X_4$ is N or a group represented by C—$(Ar_4)_d$—$R_4$; $X_5$ is N or a group represented by C—$(Ar_5)_e$—$R_5$; and $X_6$ is N or a group represented by C—$(Ar_6)_f$—$R_6$ where $Ar_1$ to $Ar_6$ are each independently a substituted or unsubstituted $C_6$-$C_{30}$ arylene group or a substituted or unsubstituted $C_2$-$C_{30}$ heteroarylene group, with the proviso that at least one of $X_1$ to $X_6$ is N.

In particular, $X_1$, $X_3$ and $X_5$ may be N; $X_1$, $X_3$ and $X_4$ may be N; $X_1$ and $X_3$ may be N; $X_1$ and $X_4$ may be N; or $X_1$ may be N.

In more particular, the compound of Formula 1 may be one of the compounds represented by Formulae 1a to 1e below:

Formula 1a

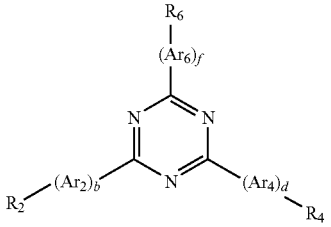

Formula 1b

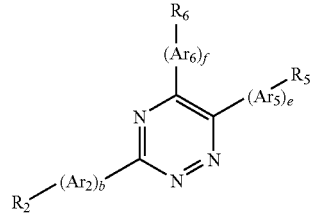

Formula 1c

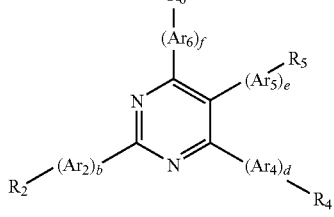

Formula 1d

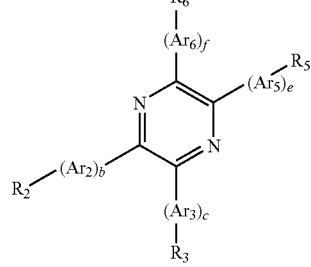

Formula 1e

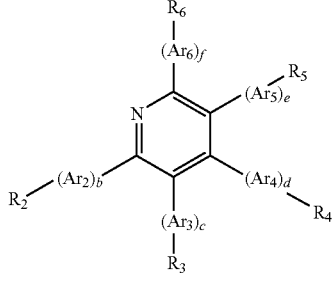

In Formula 1 and Formulae 1a to 1e, $Ar_1$ to $Ar_6$ may be each independently a substituted or unsubstituted $C_6$-$C_{30}$ arylene group or a substituted or unsubstituted $C_2$-$C_{30}$ heteroarylene group.

In particular, $Ar_1$ to $Ar_6$ may be each independently selected from the group consisting of a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylenylene group, a substituted or unsubstituted fluorenylene group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted benzofuranylene group, a substituted or unsubstituted thiophenylenylene group, a substituted or unsubstituted benzothiophenylene group, a substituted or unsubstituted isothiazolylene group, a substituted or unsubstituted isoxazolylene group, and a substituted or unsubstituted triazolylene group.

When at least one of $Ar_1$ to $Ar_6$ is a substituted $C_6$-$C_{30}$ arylene group or a substituted $C_2$-$C_{30}$ heteroarylene group, at least one of the substituents of the substituted $C_6$-$C_{30}$ aromatic ring system or the substituted $C_2$-$C_{30}$ hetero aromatic ring system may be each independently a halogen atom, a hydroxyl group, a cyano group, a substituted or unsubstituted $C_1$-$C_{30}$ alkyl group, a substituted or unsubstituted $C_1$-$C_{30}$ alkoxy group, a substituted or unsubstituted $C_1$-$C_{30}$ acyl group, a substituted or unsubstituted $C_2$-$C_{30}$ alkenyl group, a substituted or unsubstituted $C_2$-$C_{30}$ alkynyl group, a substituted or unsubstituted $C_6$-$C_{30}$ aryl group, or a substituted or unsubstituted $C_2$-$C_{30}$ heteroaryl group.

In particular, the substituent may be a halogen atom, a hydroxyl group, a cyano group, a $C_1$-$C_{10}$ alkyl group, a $C_1$-$C_{10}$ alkoxy group, a $C_1$-$C_{10}$ acyl group, a $C_2$-$C_{10}$ alkenyl group, a $C_2$-$C_{10}$ alkynyl group, a $C_6$-$C_{14}$ aryl group, or a $C_2$-$C_{14}$ heteroaryl group.

In more particular, $Ar_1$ to $Ar_6$ may be each independently a phenylene group, a phenylene group substituted with at least one cyano group, a phenylene group substituted with at least one $C_1$-$C_{10}$ alkyl group, a naphthalene group, a naphthalene group substituted with at least one cyano group, a naphthalene group substituted with at least one $C_1$-$C_{10}$ alkyl group, a fluorenylene group, or a fluorenylene group substituted with at least one $C_1$-$C_{10}$ alkyl group, a carbazolylene group, a carbazolylene group substituted with at least one phenyl group, a pyridinylene group, a triazolylene group, or a triazolylene group substituted with at least one phenyl group.

$Ar_1$ to $Ar_6$ may be each independently one of the groups represented by Formulae 2a to 2p below, but are not limited thereto:

Formula 2a

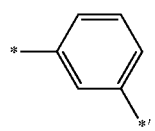

Formula 2b

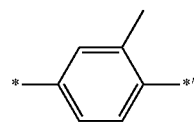

Formula 2c

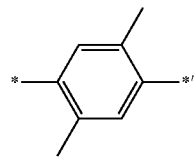

Formula 2d

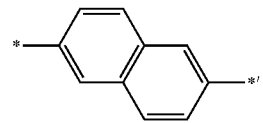

Formula 2e

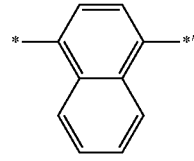

Formula 2f

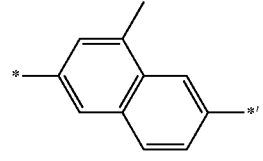

Formula 2g

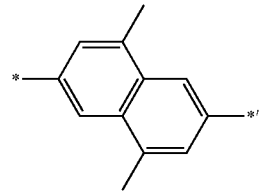

Formula 2h

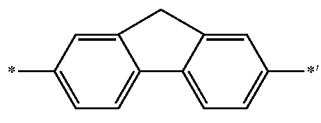

Formula 2i

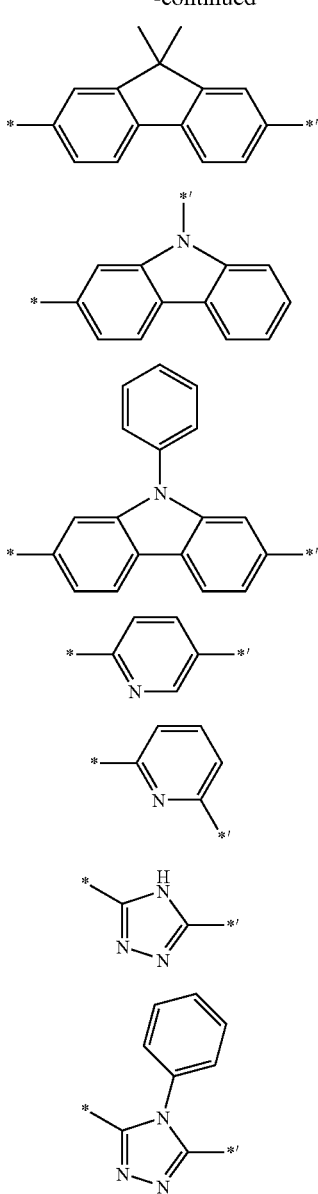

Formula 2j

Formula 2k

Formula 2l

Formula 2m

Formula 2n

Formula 2o

Formula 2p

Herein, * indicates a site bounding to C which is a cyclic element of a 6-membered aromatic ring shown in Formula 1, and *' indicates a site bounding to one of $R_1$ to $R_6$.

In Formula 1, a, b, c, d, e and f indicate the number of $Ar_1$ to $Ar_6$, and may be an integer of 0 to 10. If a, b, c, d, e and f are each independently 0, $R_1$ to $R_6$ may be directly connected to a cyclic element of a 6-membered aromatic ring shown in Formula 1. If a is 2 or greater, at least two $Ar_1$s may be the same or different. If b is 2 or greater, at least two $Ar_2$s may be the same or different. If c is 2 or greater, at least two $Ar_3$s may be the same or different. If d is 2 or greater, at least two $Ar_4$s may be the same or different. If e is 2 or greater, at least two $Ar_5$s may be the same or different. If f is 2 or greater, at least two $Ar_6$s may be the same or different. Particularly, a, b, c, d, e and f may be each independently 0, 1, 2 or 3.

In Formula 1, $R_1$ to $R_6$ may be each independently a hydrogen atom, a halogen atom, a hydroxyl group, a cyano group, a substituted or unsubstituted $C_1$-$C_{30}$ alkyl group, a substituted or unsubstituted $C_1$-$C_{30}$ alkoxy group, a substituted or unsubstituted $C_1$-$C_{30}$ acyl group, a substituted or unsubstituted $C_2$-$C_{30}$ alkenyl group, a substituted or unsubstituted $C_2$-$C_{30}$ alkynyl group, a substituted or unsubstituted $C_6$-$C_{30}$ aryl group, or a substituted or unsubstituted $C_2$-$C_{30}$ heteroaryl group. In this regard, at least two adjacent groups of $R_1$ to $R_6$ may be bonded to each other to form a saturated or unsaturated ring.

In particular, $R_1$ to $R_6$ may be each independently a hydrogen atom, a halogen atom, a hydroxyl group, a cyano group, a substituted or unsubstituted $C_1$-$C_{10}$ alkyl group, a substituted or unsubstituted $C_2$-$C_{10}$ alkoxy group, a substituted or unsubstituted $C_1$-$C_{10}$ acyl group, a substituted or unsubstituted $C_2$-$C_{10}$ alkenyl group, a substituted or unsubstituted $C_2$-$C_{10}$ alkynyl group, a substituted or unsubstituted $C_6$-$C_{14}$ aryl group, or a substituted or unsubstituted $C_2$-$C_{14}$ heteroaryl group.

More particularly, $R_1$ to $R_6$ may be each independently a halogen atom, a hydroxyl group, a cyano group, a $C_1$-$C_{10}$ alkyl group, a $C_6$-$C_{14}$ aryl group, a $C_6$-$C_{14}$ aryl group substituted with a cyano group, a $C_6$-$C_{14}$ aryl group substituted with at least one $C_1$-$C_{10}$ alkyl group, a $C_2$-$C_{14}$ a heteroaryl group, a $C_2$-$C_{14}$ heteroaryl group substituted with a cyano group, a $C_2$-$C_{14}$ heteroaryl group substituted with at least one $C_1$-$C_{10}$ alkyl group, or a $C_2$-$C_{14}$ heteroaryl group substituted with at least one phenyl group.

$R_1$ to $R_6$ may be each independently a hydrogen atom or one of the groups represented by Formulae 3a to 3q below, but are not limited thereto:

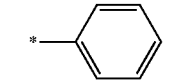

Formula 3a

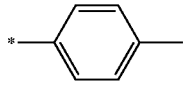

Formula 3b

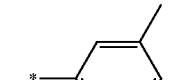

Formula 3c

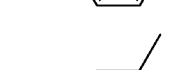

Formula 3d

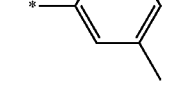

Formula 3e

Formula 3f

Formula 3g

Herein, * indicates a site bounding to C which is a cyclic element of a 6-membered aromatic ring shown in Formula 1, or a site bounding to one of $Ar_1$ to $Ar_6$.

In Formula 1, the group represented by $-(Ar_1)_a-R_1$, the group represented by $-(Ar_2)_b-R_2$, the group represented by $-(Ar_3)_c-R_3$, the group represented by $-(Ar_4)_d-R_4$, the group represented by $-(Ar_5)_e-R_5$, and the group represented by $-(Ar_6)_f-R_6$ may be each independently one of the groups represented by Formulae 4a to 4y below, but are not limited thereto:

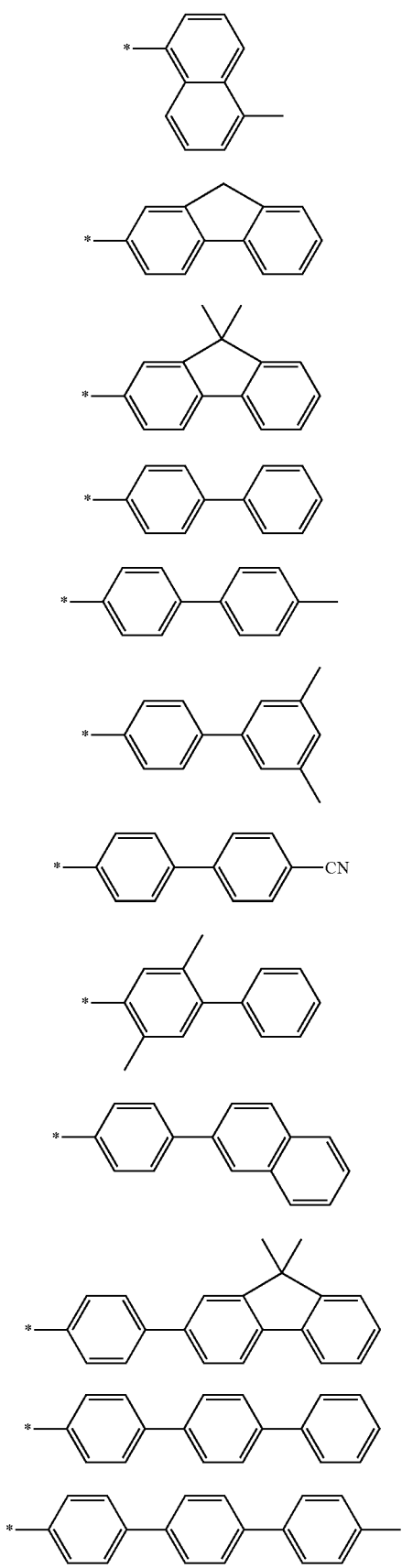
Formula 4i
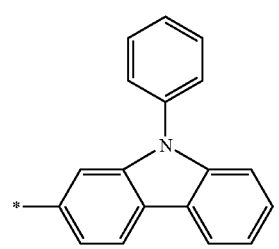
Formula 4u
Formula 4j
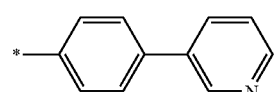
Formula 4v
Formula 4k
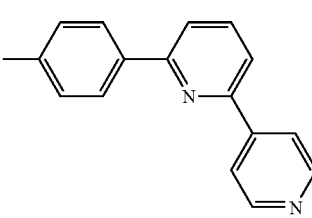
Formula 4w
Formula 4l
Formula 4m
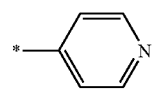
Formula 4x
Formula 4n
Formula 4y
Formula 4o
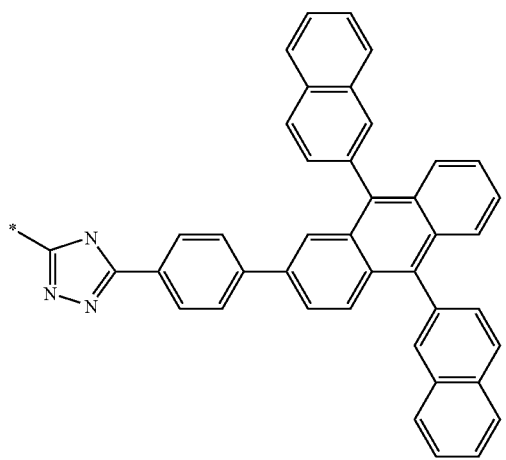
Formula 4p
Formula 4q
The compound represented by Formula 1 may be one of the compounds represented by Formulae 5 to 39 below (which are also referred to as Compounds 1 to 35, respectively), but is not limited thereto:
Formula 4r
Formula 5
Formula 4s
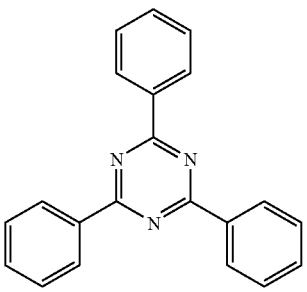
Formula 4t Formula 6
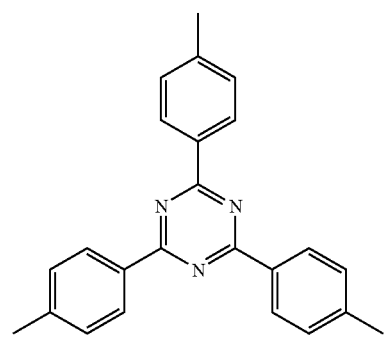
Formula 7
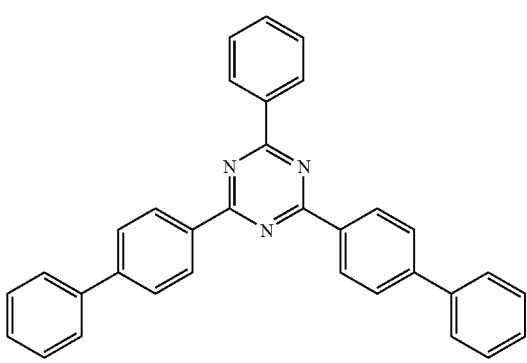
Formula 8
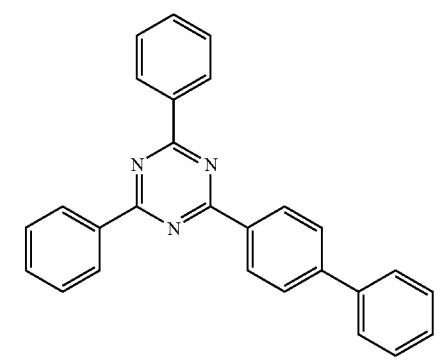
Formula 9
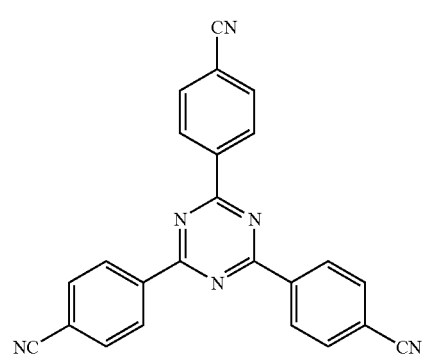
Formula 10
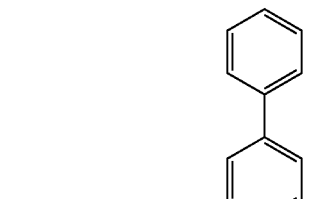
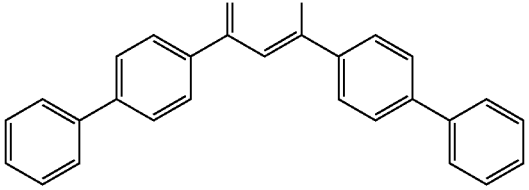
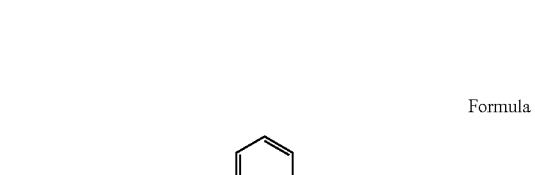
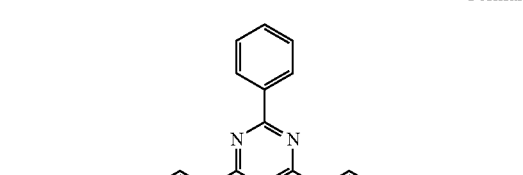
Formula 11
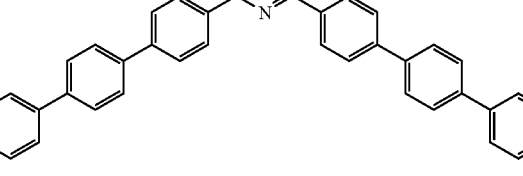
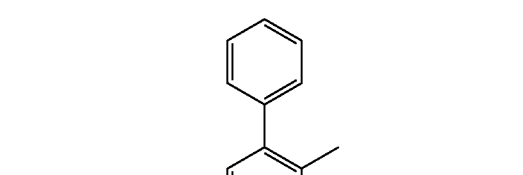
Formula 12
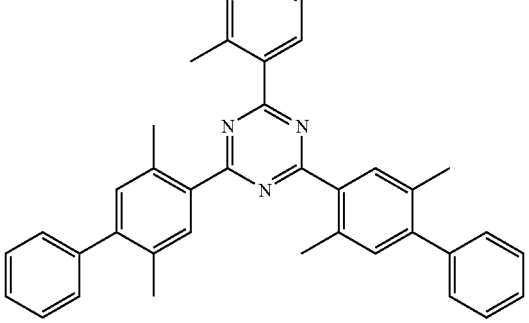

Formula 13
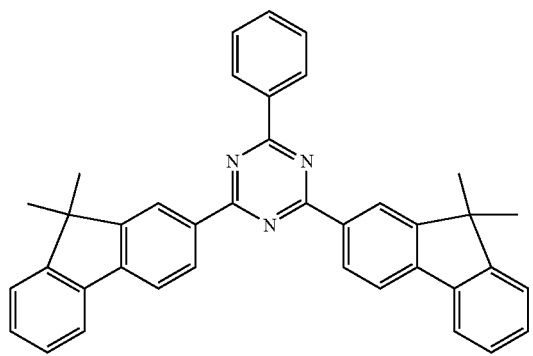
Formula 14
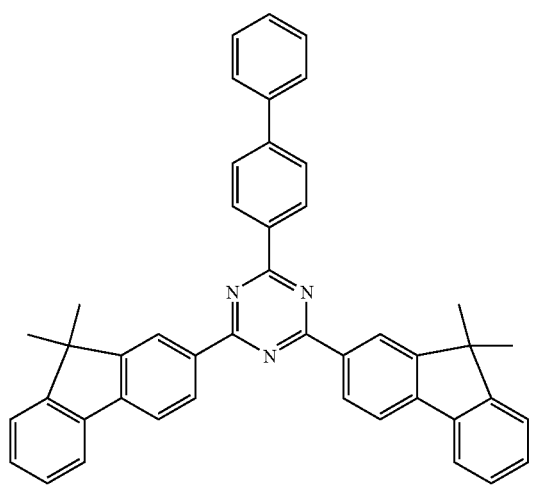
Formula 15
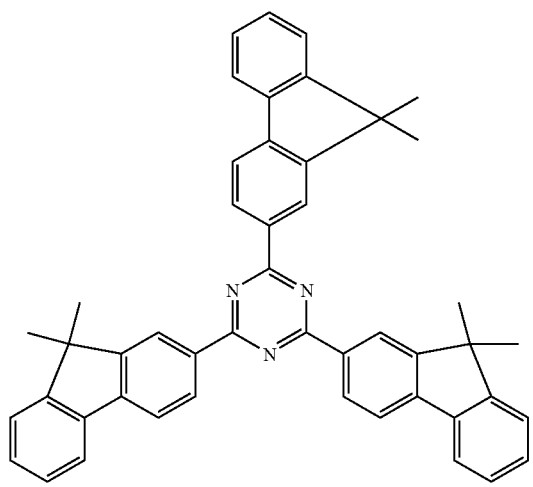
Formula 16
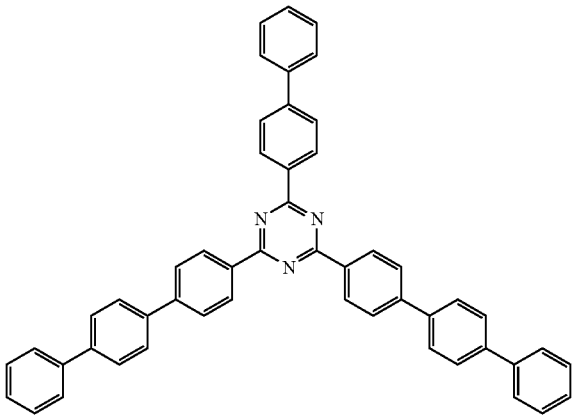
Formula 17
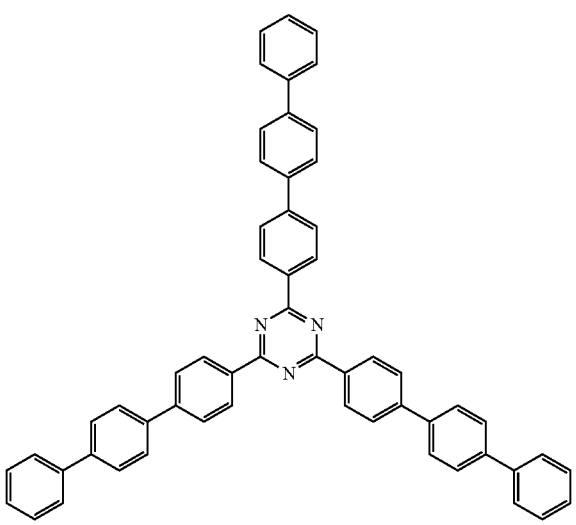
Formula 18
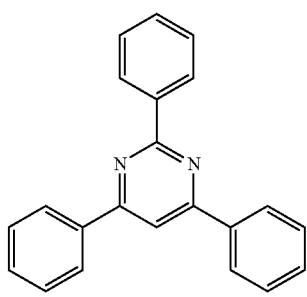
Formula 19
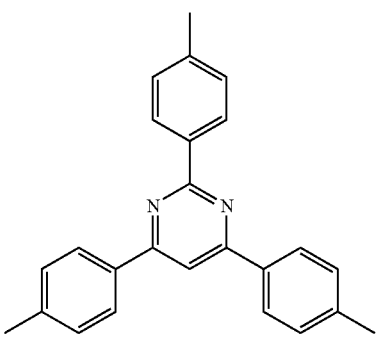

Formula 20
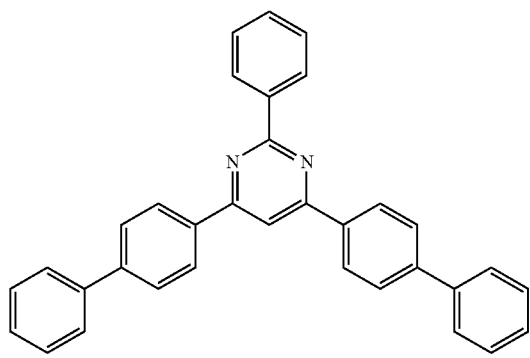
Formula 21
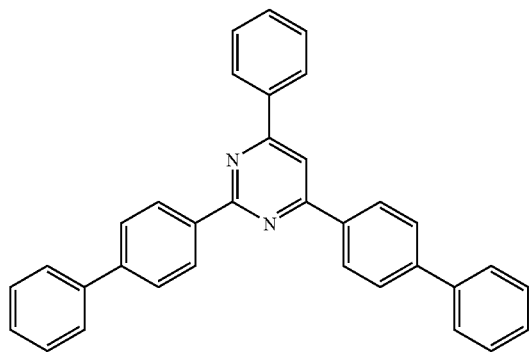
Formula 22
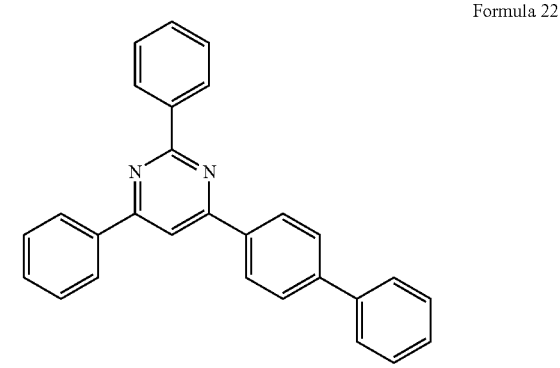
Formula 23
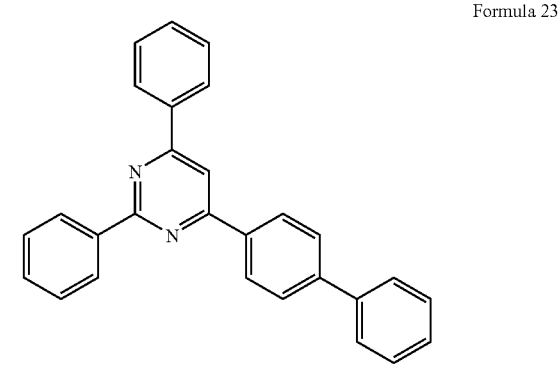
Formula 24
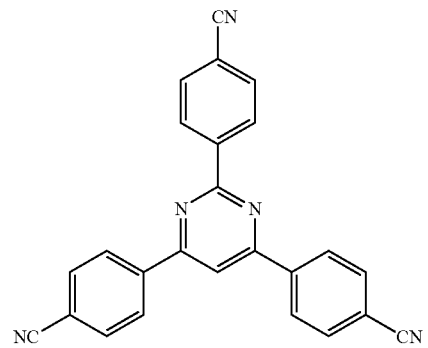
Formula 25
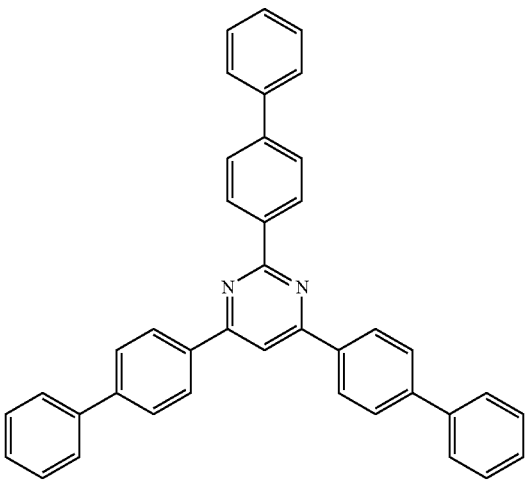
Formula 26
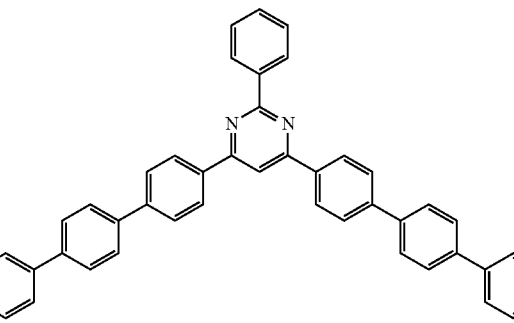
Formula 27
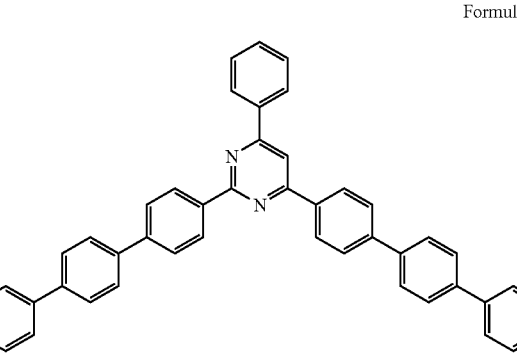

Formula 28
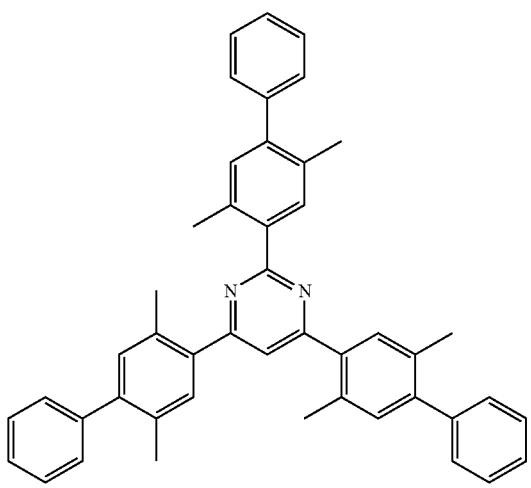
Formula 31
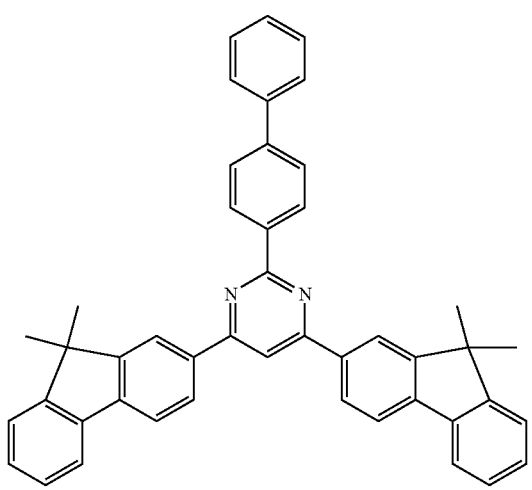
Formula 29
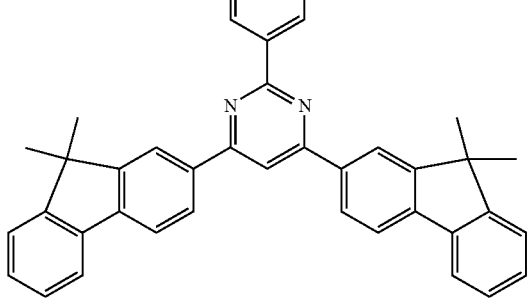
Formula 32
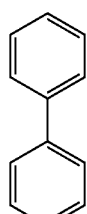
Formula 30
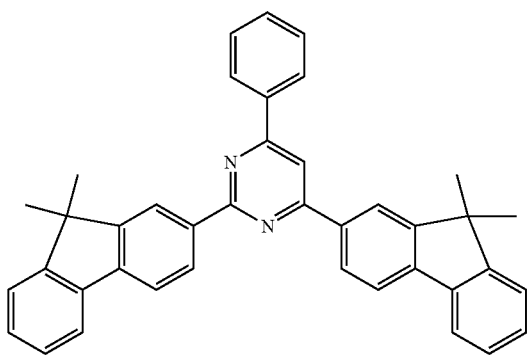
Formula 33
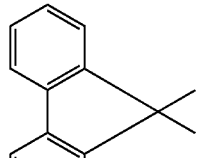

Formula 34

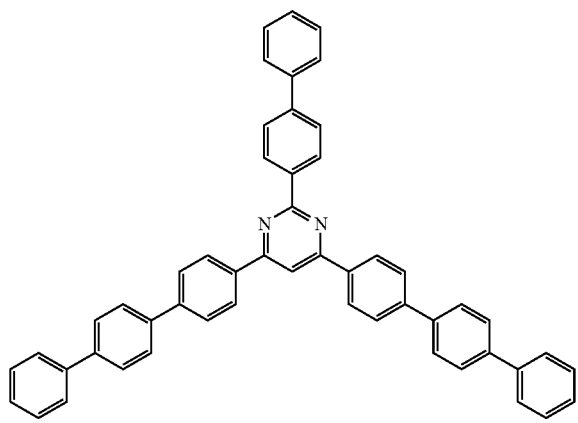

Formula 35

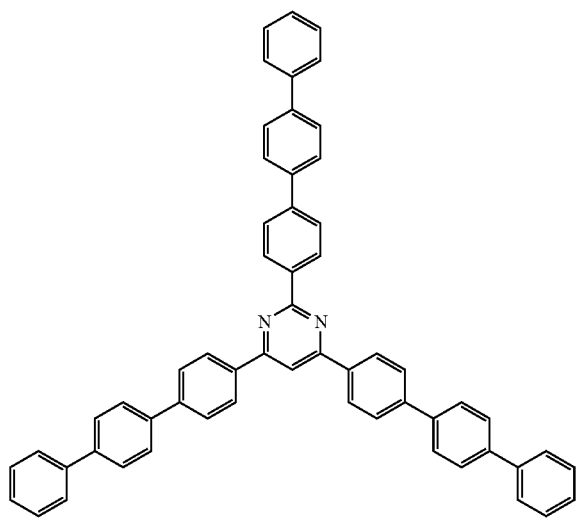

Formula 36

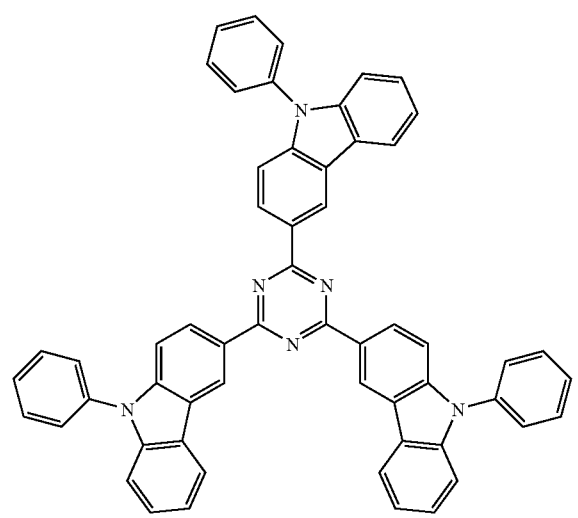

Formula 37

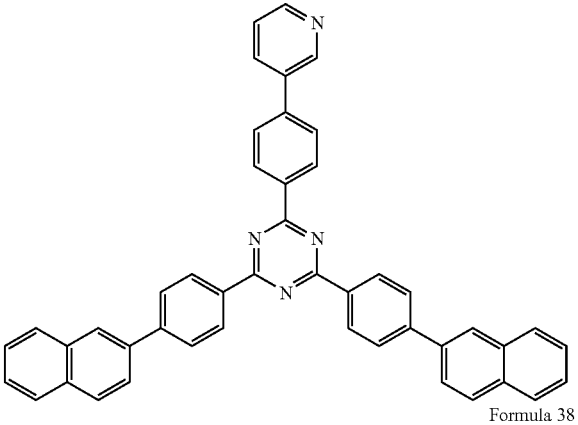

Formula 38

Formula 39

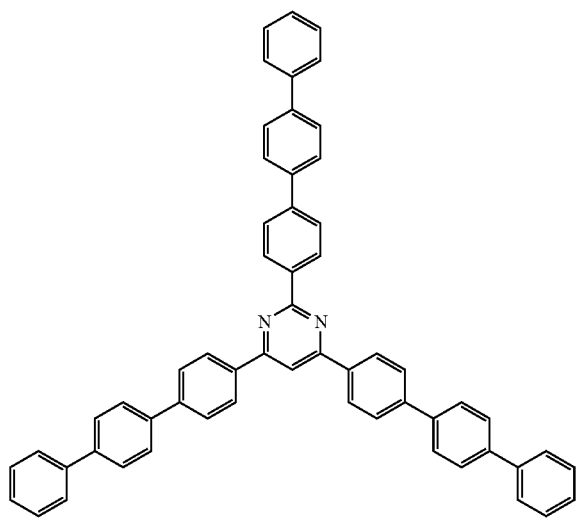

Examples of the unsubstituted $C_1$-$C_{30}$ alkyl group described in the specification are a methyl group, an ethyl group, a propyl group, an isobutyl group, a sec-butyl group, a pentyl group, an iso-amyl group, and a hexyl group, wherein at least one of the hydrogen atoms in the alkyl group may be substituted with a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{30}$ alkyl group, a $C_1$-$C_{30}$ alkenyl group, a $C_1$-$C_{30}$ alkynyl group, a $C_6$-$C_{30}$ aryl group, a $C_7$-$C_{20}$ arylalkyl group, a $C_2$-$C_{20}$ heteroaryl group, or a $C_3$-$C_{30}$ heteroarylalkyl group.

The unsubstituted $C_1$-$C_{30}$ alkoxy group described in the specification may be a group represented by -OA, wherein A is a $C_1$-$C_{30}$ alkyl group. Examples of the $C_1$-$C_{30}$ alkoxy group are a methoxy group, an ethoxy group, and an isopropyloxy group. At least one of the hydrogen atoms in the alkoxy group may be subsitued with the substituents described with reference to the alkyl group.

Examples of the unsubstituted $C_1$-$C_{30}$ acyl group described in the specification may be an acetayl group, an ethyl carbonyl group, an isopropyl carbonyl group, a phenyl carbonyl group, a naphthalene carbonyl group, a diphenyl carbonyl group, a cyclohexyl carbonyl group, or the like. At least one of the hydrogen atoms in the acyl group may be substituted with the substituents described with reference to the alkyl group.

The unsubstituted $C_2$-$C_{30}$ alkenyl group described in the specification is a hydrocarbon chain having a carbon-carbon double bond in the center or at one end of the alkyl group structure. Examples of the unsubstituted $C_2$-$C_{30}$ alkenyl group are an ethenyl group, a propenyl group, and a butenyl group. At least one hydrogen atom in the alkenyl group may be substituted with the substituents described with reference to the alkyl group.

The $C_2$-$C_{30}$ alkynyl group described in the specification is a hydrocarbon chain having a carbon-carbon triple bond in the center or at one end of the alkyl group structure. Examples of the $C_2$-$C_{30}$ alkynyl group are an acetylene group, a propylene group, a phenylacetylene group, a naphthylacetylene group, an isopropylacetylene group, a t-butylacetylene group, and a diphenylacetylene group. At least one hydrogen atom in the alkynyl group may be substituted with the substituents described with reference to the alkyl group.

The unsubstituted $C_6$-$C_{30}$ aryl group described in the specification is a monovalent group having a carbocyclic aromatic system having 6 to 30 carbon atoms including at least one aromatic ring. The unsubstituted $C_6$-$C_{30}$ arylene group is a bivalent group having a carbocyclic aromatic system having 6 to 30 carbon atoms including at least one aromatic ring. When the aryl group and the arylene group have at least two rings, they may be fused to each other or bonded to each other via a single bond. At least one hydrogen atom in the aryl group and the arylene group may be substituted with the substituents described with reference to the alkyl group.

Examples of the substituted or unsubstituted $C_6$-$C_{30}$ aryl group may be a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene) phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphtylenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, or an ovalenyl group. Examples of the substituted or unsubstituted $C_6$-$C_{30}$ arylene group may be easily derived from examples of the substituted or unsubstituted $C_6$-$C_{30}$ aryl group.

The unsubstituted $C_2$-$C_{30}$ heteroaryl group described in the specification is a monovalent group having at least one aromatic ring having at least one of the heteroatoms selected from the group consisting of N, O, P, and S. The unsubstituted $C_2$-$C_{30}$ heteroarylene group described in the specification is a bivalent group having at least one aromatic ring having at least one of the heteroatoms selected from the group consisting of N, O, P, and S. If the heteroaryl group and the heteroarylene group have at least two rings, they may be fused each other or bonded to each other via a single bond. At least one hydrogen atom in the heteroaryl group and the heteroarylene group may be substituted with the substituents described with reference to the alkyl group.

Examples of the unsubstituted $C_2$-$C_{30}$ heteroaryl group may be a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, or the like. Examples of the unsubstituted $C_2$-$C_{30}$ heteroarylene group may be easily derived from examples of the substituted or unsubstituted $C_6$-$C_{30}$ arylene group.

Since the luminescent efficiency improvement layer 18 including the compound of Formula 1 described above has a high refractive index, an OLED including the luminescent efficiency improvement layer 18 may have excellent luminescent efficiency, particularly external luminescent efficiency. For example, the luminescent efficiency improvement layer 18 may have a refractive index of 1.8 or greater, and preferably 1.9 at a wavelength of 630 nm.

Since an OLED generally has a structure in which a plurality of layers formed of various materials are stacked, light generated in the organic layer may not be emitted outside of the OLED by reflection so that the light may be dissipated within the OLED while the light is passing through the layers. In an OLED having low external luminescent efficiency, the total luminescent efficiency of the OLED may be reduced even if conversion efficiency of light is high in the organic layer. However, the luminescent efficiency improvement layer 18 improves external luminescent efficiency by constructive interference while light generated in the organic layer is passing through the second electrode 17. Thus, luminescent efficiency of the OLED 10 according to the present embodiment may be significantly improved.

According to FIG. 1, the luminescent efficiency improvement layer 18 is formed on the second surface of the second electrode 17, but if required, a variety of layers may be formed between the luminescent efficiency improvement layer 18 and the second electrode 17. Meanwhile, even though not shown in FIG. 1, a sealing layer may further be formed on the luminescent efficiency improvement layer 18 in order to seal the OLED 10, and various modifications may be applied thereto.

Figure 2:
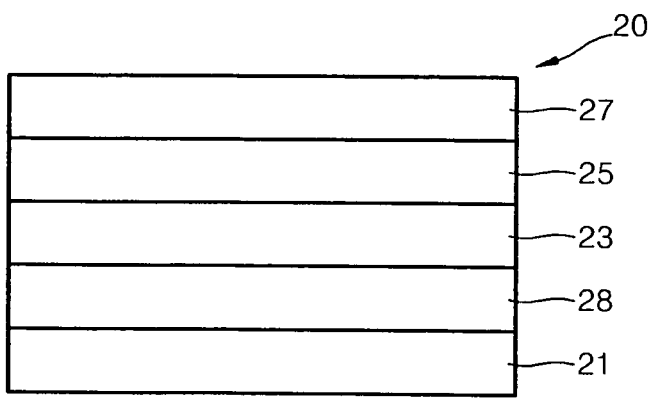
FIG. 2 is a schematic sectional view of an OLED according to another embodiment of the present invention.

FIG. 2 is a schematic sectional view of an OLED 20 according to another embodiment of the present invention. Referring to FIG. 2, the OLED 20 according to the present embodiment includes a substrate 21, a luminescent efficiency improvement layer 28, a first electrode 23, an organic layer 25 and a second electrode 27, which are sequentially stacked in this order. The first electrode 23 is a transmission electrode, and light generated in the organic layer 25 passes through the first electrode 23 and the luminescent efficiency improvement layer 28 and is transmitted out of the OLED 20. The first electrode 23 has a first surface contacting with the organic layer 25 and a second surface being opposite to the organic layer 25. The luminescent efficiency improvement layer 28 is formed on the second surface of the first electrode 23 as shown in FIG. 2. In other words, the luminescent efficiency improvement layer 28 is positioned below the second surface of the first electrode 23. If required, a variety of layers may be formed between the luminescent efficiency improvement layer 28 and the first electrode 23. The layers of the OLED 20 are the same as those of the OLED 10, and thus detailed descriptions thereof will not be provided here. Since the luminescent efficiency improvement layer 28 including the compound of Formula 1 has a high refractive index, light generated in the organic layer 25 may be efficiently transmitted out of the OLED by the constructive interference effect. Thus, luminescent efficiency of the OLED 20 may be improved.

Figure 3:
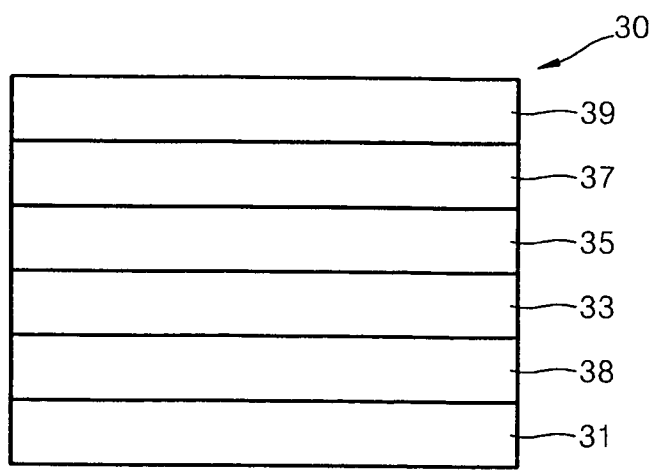
FIG. 3 is a schematic sectional view of an OLED according to another embodiment of the present invention.

FIG. 3 is a schematic sectional view of an OLED 30 according to another embodiment of the present invention. Referring to FIG. 3, the OLED 30 according to the present embodiment includes a substrate 31, a first luminescent efficiency improvement layer 38, a first electrode 33, an organic layer 35, a second electrode 37, and a second luminescent efficiency improvement layer 39, which are sequentially stacked in this order. In the OLED 30, the first electrode 31 and the second electrode 37 are transmission electrodes. Light generated in the organic layer 35 passes through the first electrode 31 and the first luminescent efficiency improvement layer 38 before being transmitted out of the OLED 30. The light also passes through the second electrode 37 and the second luminescent efficiency improvement layer 39 before being transmitted out of the OLED 30. The layers of the OLED 30 are the same as those of the OLED 10 and OLED 20, and thus detailed descriptions thereof will not be provided here. Since each of the first luminescent efficiency improvement layer 38 and the second luminescent efficiency improvement layer 39 having the compound of Formula 1 has a high refractive index, light generated in the organic layer 35 may be efficiently transmitted out of the OLED 30 according to the constructive interference effect. Thus, luminescent efficiency of the OLED 30 may be improved.

The organic layer of the OLED according to an embodiment of the present invention may be patterned according to R, G and B pixels. Thus, the organic layer may include a red organic layer, a green organic layer, and a blue organic layer.

The luminescent efficiency improvement layer including the compound of Formula 1 may be formed as a common layer with respect to the R, G and B pixels. The luminescent efficiency improvement layer as a common layer may have a thickness of 500 to 800 Å, and preferably 600 to 700 Å. If the thickness of the luminescent efficiency improvement layer is within the range described above, excellent luminescent efficiency may be obtained.

Alternatively, the luminescent efficiency improvement layer may be at least one of a luminescent efficiency improvement layer -R, a luminescent efficiency improvement layer -G and a luminescent efficiency improvement layer -B. That is, the luminescent efficiency improvement layer may be patterned according to R, G and B pixels.

The term "luminescent efficiency improvement layer -R" used herein is a luminescent efficiency improvement layer formed in a region corresponding to the R pixel.

The term "luminescent efficiency improvement layer -G" used herein is a luminescent efficiency improvement layer formed in a region corresponding to the G pixel.

The term "luminescent efficiency improvement layer -B" used herein is a luminescent efficiency improvement layer formed in a region corresponding to the B pixel.

According to an embodiment of the present invention, the luminescent efficiency improvement layer -R, the luminescent efficiency improvement layer -G, and the luminescent efficiency improvement layer -B may be formed on at least one of the second surface of the second electrode and the second surface of the first electrode.

The thicknesses of the luminescent efficiency improvement layer -R, the luminescent efficiency improvement layer -G, and the luminescent efficiency improvement layer -B may be the same or different.

Hereinafter, the present invention will be described in greater detail with reference to the following examples. The following examples are for illustrative purposes only and are not intended to limit the scope of the invention.

EXAMPLES

Synthesis Example 1

Synthesis of Compound 11

Compound 11 was synthesized through Reaction Scheme 1 below:

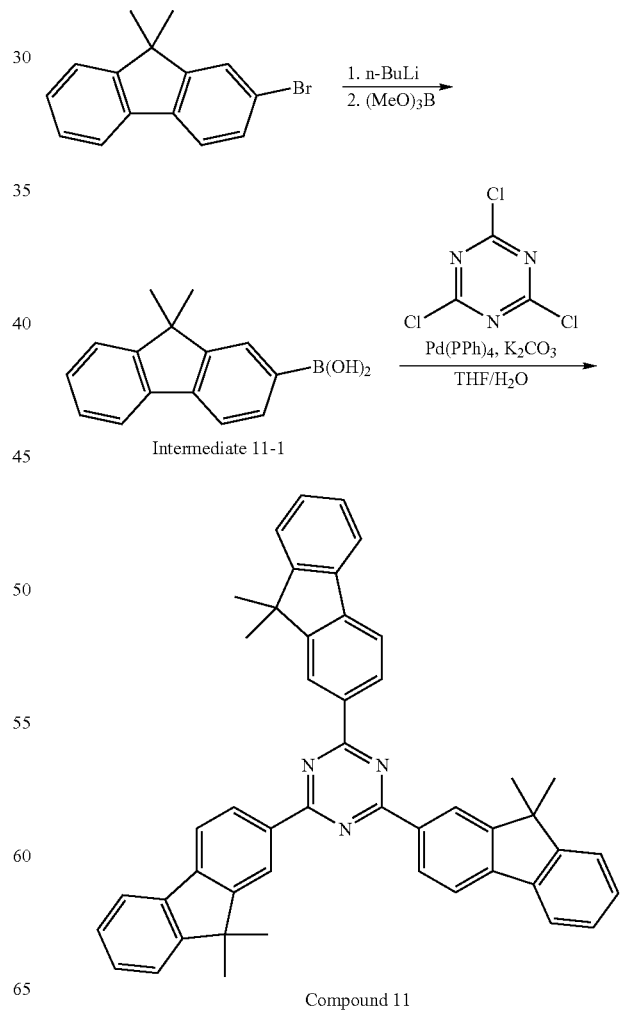

Synthesis of Intermediate 11-1

20 g (73.2 mmol) of bromo dimethyl fluorene was dissolved in tetrahydrofuran (THF) in a 500 mL flask, and 32 mL (80 mmol) of 2.5M n-butyllithium (n-BuLi) was gradually added thereto at −78° C. After one hour, 22 g of trimethyl borate was added thereto. 1N hydrochloric acid was added thereto, and the mixture was stirred for 2 hours and subjected to extraction with ethyl acetate. The resultant was dried and purified using a silicagel column chromatography to obtain pure Intermediate 11-1.

Synthesis of Compound 11 Represented by Formula 15

10 g of Intermediate 11-1, 2.3 g of cyanuric chloride, and 2.4 g of tetrakis(triphenylphospine)palladium (Pd(PPh)$_4$) were dissolved in THF, and 200 mL of 1M potassium carbonate (K$_2$CO$_3$) solution was added thereto. The mixture was refluxed for 12 hours. Then, the resultant was subjected to extraction using ethyl acetate, dried, and purified using a silicagel column chromatography to obtain pure Compound 11.

$^1$H NMR (400 MHz, CDCl$_3$) 8.12 (3H), 7.84 (3H), 7.78 (3H), 7.62-7.56 (6H), 7.28-7.23 (6H), 1.62 (18H)

Synthesis Example 2

Synthesis of Compound 32

Compound 32 represented by Formula 36 was synthesized through Reaction Scheme 2 below:

Reaction Scheme 2

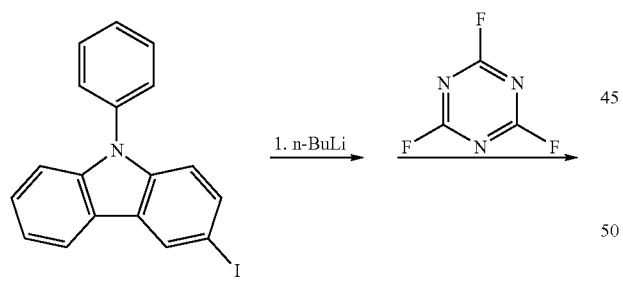

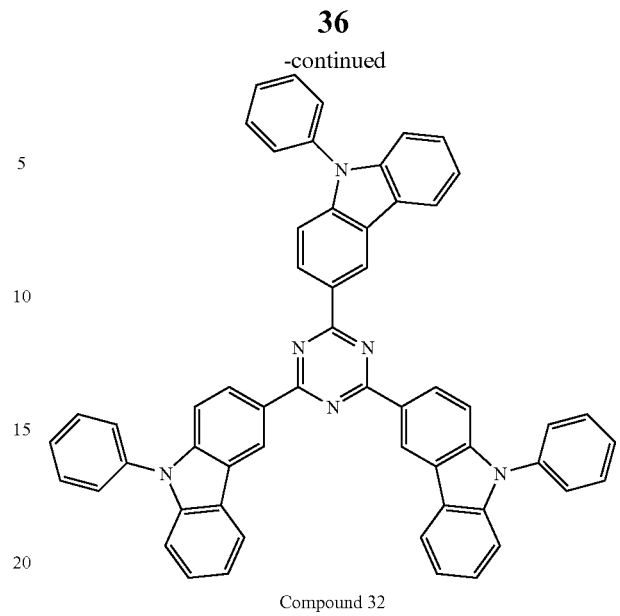

Compound 32

10 g of 3-iodine-9-phenyl carbazole was dissolved in THF, and the solution was cooled to −78° C. 12 mL of 2.5 M n-BuLi was gradually added thereto, and the mixture was stirred for 1 hour. 1.2 g cyanuric fluride dissolved in THF was gradually added thereto. After stirring for 4 hours, an ammonium chloride solution was added thereto, and the resultant was subjected to extraction using ethyl acetate. The resultant was dried and purified using a silicagel column chromatography to obtain pure Compound 32.

$^1$H NMR (400 MHz, CDCl$_3$) 7.82 (3H), 7.54 (3H), 7.48-7.39 (6H), 7.29 (18H), 7.09-7.01 (6H)

Synthesis Example 3

Synthesis of Compound 33

Compound 33 Represented by Formula 37 was Synthesized through Reaction Scheme 3 below:

Reaction Scheme 3

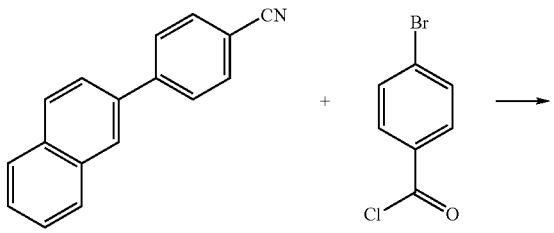

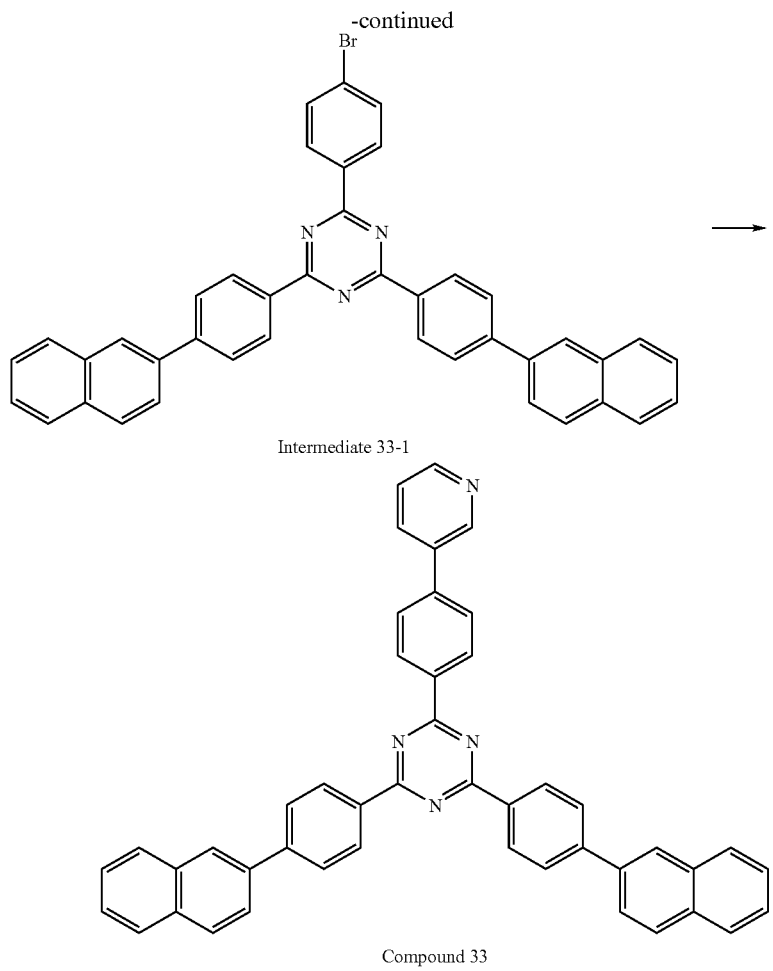

Intermediate 33-1

Compound 33

Synthesis of Intermediate 33-1

5 g (21.8 mmol) of 4-naphthalen-2-yl-benzonitrile and 2.66 g (12.1 mmol) of 4-bromobenzoyl chloride were dissolved in 200 mL chloroform, and 1.55 mL (12.1 mmol) of $SbCl_5$ was added thereto at 0° C. The mixture was stirred for 1 hour and refluxed for 12 hours at room temperature. Then, chloroform was removed under reduced pressure, and 300 mL of 28% ammonium hydroxide solution was added thereto at 0° C. Then, white precipitate was formed. The precipitate was stirred for 1 hour at room temperature, filtered and washed with water and methanol. The resultant was dried in a vacuum oven, chloroform was added thereto, and the mixture was refluxed while heating. The resultant was filtered and dried under reduced pressure to obtain 4.96 g of white solid Intermediate 33-1 (Yield: 64%).

Synthesis of Compound 33

5.75 g (8.98 mmol) of Intermediate 33-1 and 1.1 g (8.98 mmol) of 3-pyridine boronic acid were dissolved in a mixture of THF and 3.72 g of potassium carbonate solution, and 310 mg of tetrakis(triphenylphospine)palladium was added thereto. The mixture was refluxed for 12 hours while heating. The mixture was cooled to room temperature, and water was added thereto. The mixture was subjected to extraction using ethyl acetate and dried using anhydrous magnesium sulfate, and the solvent was dried under reduced pressure. Methanol was added to the resultant to form 4.5 g of white solid Compound 33 (Yield: 78%)

$^1$H NMR (400 MHz, $CDCl_3$) 8.93 (1H), 8.80 (6H), 8.61 (1H), 8.10 (2H), 7.92-7.65 (15H), 7.52 (4H), 7.32 (1H)

Synthesis Example 4

Synthesis of Compound 34

Intermediate 34-1 was synthesized through Reaction Scheme 4-1 below:

Reaction Scheme 4-1

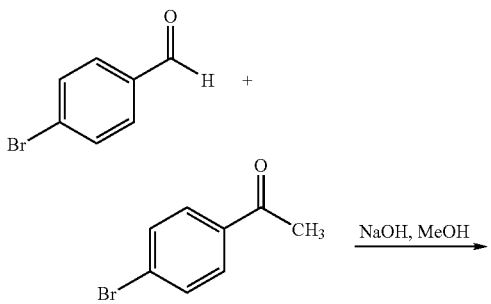

-continued

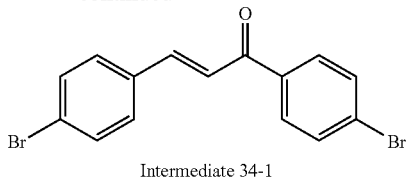
Intermediate 34-1

24.9 g (0.134 mol) of 4-bromobenzaldehyde and 26.8 g (0.134 mol) of 4-bromoacetophenone were dissolved in 120 mL of methanol in a nitrogen atmosphere. Then, 0.27 g of sodium hydroxide was added thereto, and the mixture was stirred at room temperature for 5 hours to obtain a yellow product. The yellow product was filtered, and washed with water and methanol. The resultant was dried in a vacuum oven to obtain 44.2 g of Intermediate 34-1 (Yield: 90%).

Intermediate 34-2 was synthesized through Reaction Scheme 4-2 below:

Reaction Scheme 4-2

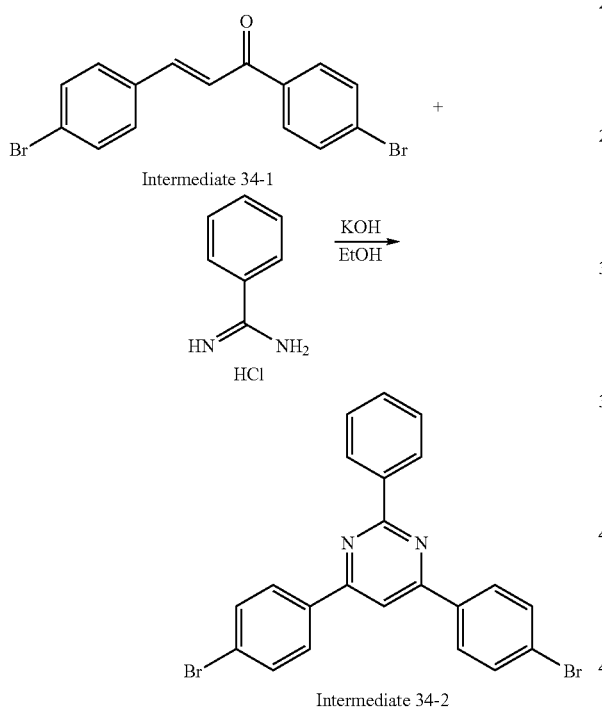

7.46 g (20.38 mmol) of 1,3-bis-(4-bromo phenyl)-propenone (Intermediate 34-1) and 1.6 g (10.19 mmol) of benzamidine hydrogen chloride were dissolved in 30 mL of anhydrous ethanol in a nitrogen atmosphere. A solution prepared by dissolving 1.32 g of potassium hydroxide in 30 ml of anhydrous ethanol was gradually added thereto for 15 minutes, and dry air was bubbled through the reaction mixture. The mixture was refluxed for 24 hours, and then mixed with water. The resultant was filtered, washed with ethanol, and dried in a vacuum oven to obtain Intermediate 34-2.

Intermediate 34-3 was Synthesized through Reaction Scheme 4-3 below:

Reaction Scheme 4-3

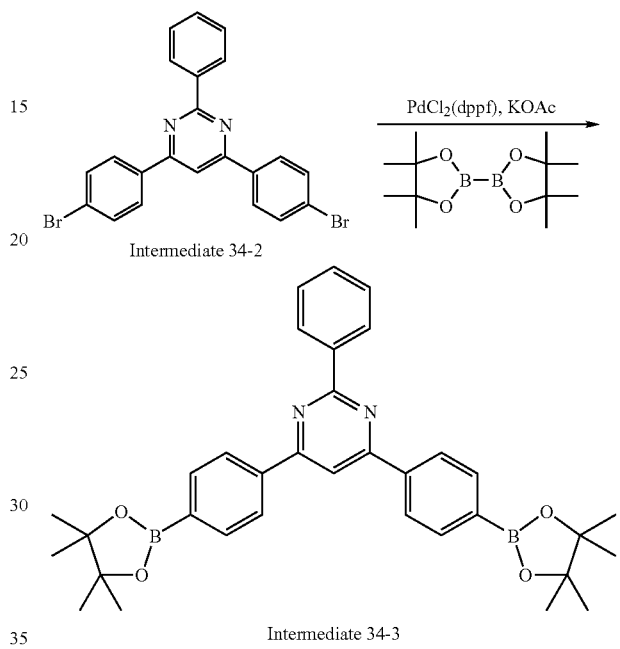

20 g (42.9 mmol) of (4,6-bis-(4-bromo-phenyl)-2-phenyl-pyrimidine)(Intermediate 34-2), 27.2 g (108 mmol) of bis(pinacolato)diboron, 25.2 g (257 mmol) of potassium acetate, 3.5 g (4.29 mmol) of $PdCl_2(dppf)$, and a solvent of anhydrous 1,4-dioxane were added to a flask, and the mixture was heated at 80° C. for 24 hours in a nitrogen atmosphere. After the reaction was completed, the resultant was filtered using sellaite as a filter, subjected to extraction using ethyl acetate, and dried using anhydrous magnesium sulfate, and the solvent was dried under reduced pressure. The resultant was purified using a column chromatography (in a developing solvent, ethyl acetate: hexane=1:4) to obtain Intermediate 34-3.

Compound 34 Represented by Formula 38 was Synthesized through Reaction Scheme 4-4 below:

Reaction Scheme 4-4

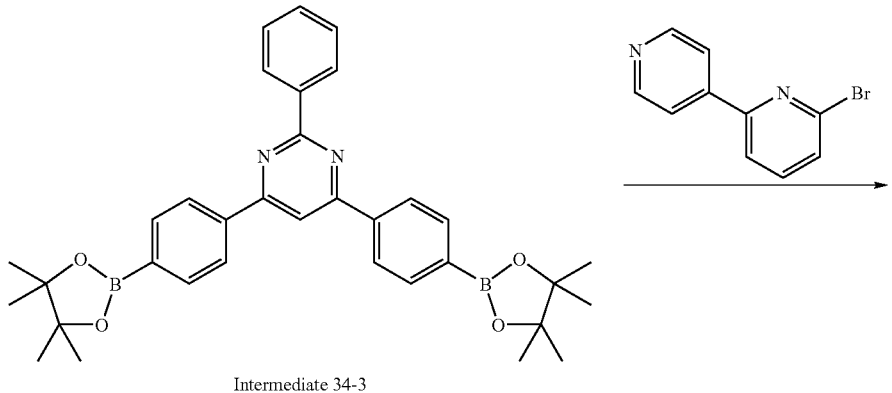
Intermediate 34-3

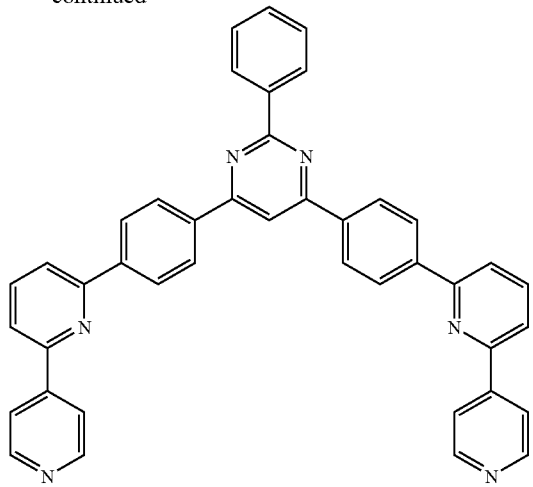

Compound 34

3.0 g (5.36 mmol) of Intermediate 34-3 and 3.15 g (13.4 mmol) of 6-bromo-(2,4')bipyridinyl were dissolved in a mixture of THF and 4.44 g of potassium carbonate, and 370 mg of tetrakis(triphenylphospine)palladium was added thereto. The mixture was refluxed for 15 hours while heating. After the reaction was completed, the mixture was cooled to room temperature, and water was added thereto. The mixture was subjected to extraction using ethyl acetate and dried using anhydrous magnesium sulfate, and the solvent was dried under reduced pressure. Methanol was added to the resultant to obtain 2.475 g of yellow solid Compound 34 (Yield: 75%).

$^1$H NMR (400 MHz, CDCl$_3$) 8.80-8.77 (6H), 8.48 (4H), 8.37 (4H), 8.16 (1H), 8.08 (4H), 7.94-7.91 (4H), 7.83 (2H), 7.60-7.55 (3H)

Synthesis Example 5

Synthesis of Compound 35

Compound 35 Represented by Formula 39 was Synthesized through Reaction Scheme 5 below:

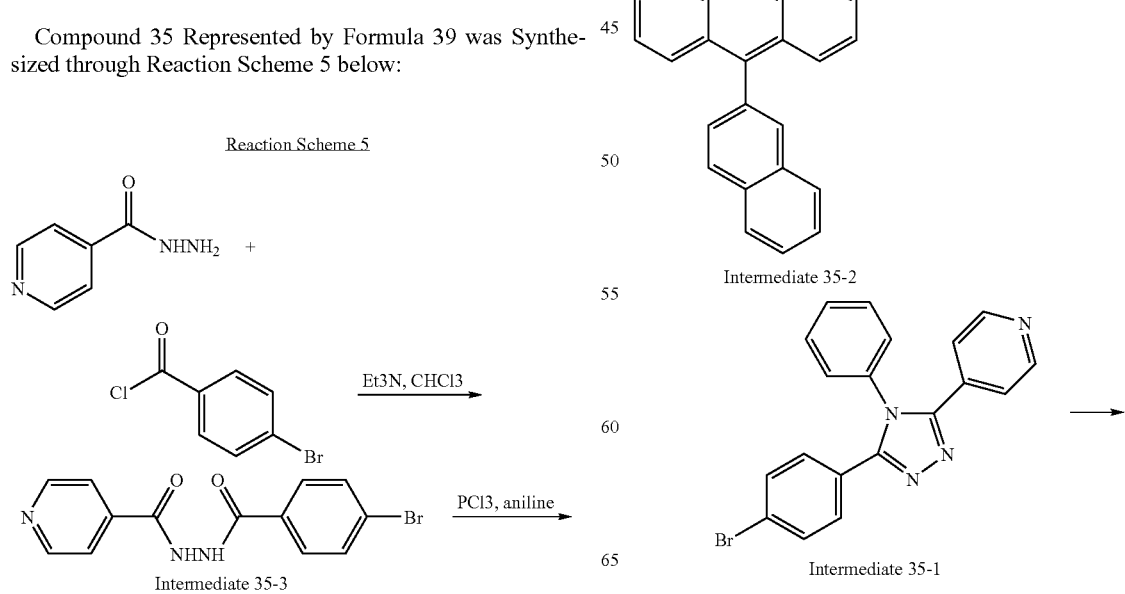

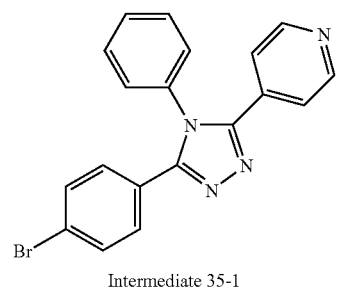

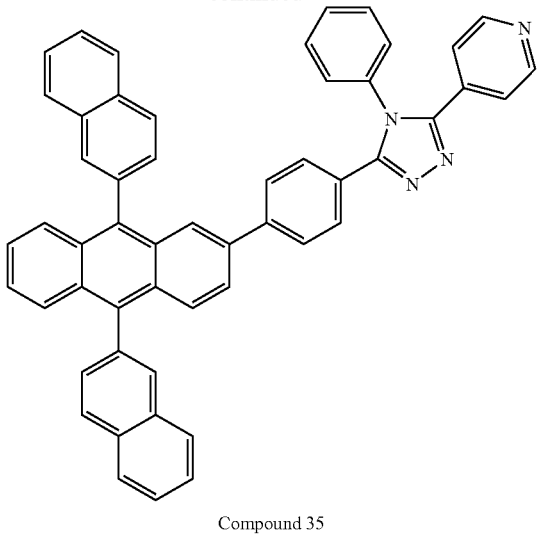 [SMILES: c1ccc(-n2c(-c3ccncc3)nnc2-c2ccc(-c3ccc4c(-c5ccc6ccccc6c5)c5ccccc5c(-c5ccc6ccccc6c5)c4c3)cc2)cc1]

Compound 35

13.7 g of isonicotinic acid hydrazide, 22 g of 4-bromobenzoyl chloride, and 10 g of triethyl amine (Et3N) were dissolved in chloroform (CHCl$_3$), and the mixture was stirred at room temperature for 2 hours. A precipitate was filtered by adding water to the mixture, and recrystallized using methanol to obtain Intermediate 35-3.

2.06 g of PCl$_3$ was added to a solution prepared by dissolving 10.3 g of aniline in 1,2-dichlorobenzene, and the mixture was stirred at 100° C. for 1 hour. 3 g of Intermediate 35-3 was added thereto, and the mixture was refluxed for 24 hours while heating at 200° C. The mixture was cooled to room temperature, and 2 N hydrochloric acid solution was gradually added thereto. The resultant was filtered using sellaite as a filter, and washed using dichloro methane. The resultant was washed with water and dried using anhydrous magnesium sulfate. Dichloro methane was removed under reduced pressure, and 1,2-dichloro benzene was removed using vacuum distillation. The resultant was purified using a column chromatography to obtain Intermediate 35-1.

19 g of Intermediate 35-1 and 24 g of Intermediate 35-2 were dissolved in a mixture of THF and 34.5 g of potassium carbonate solution, and 2.9 g of tetrakis(triphenylphospine) palladium was added thereto. The mixture was refluxed for 15 hours while heating. After the reaction was completed, the mixture was cooled to room temperature, and water was added thereto. The mixture was subjected to extraction using dichloro methane and dried using anhydrous magnesium sulfate, and the solvent was dried under reduced pressure. Methanol was added to the resultant to obtain 27 g of yellow solid Compound 35 (Yield: 75%).

$^1$H NMR (400 MHz, CDCl$_3$) 8.65 (2H), 8.15 (1H), 7.97 (1H), 7.94-7.91 (4H), 7.73-7.67 (6H), 7.61-7.54 (9H), 7.39 (2H), 7.32-7.30 (9H)

Example 1

A luminescent efficiency improvement layer was formed on a substrate to a thickness of 600 Å by vacuum depositing Compound 11 prepared in Synthesis Example 1. An anode was formed on the luminescent efficiency improvement layer by forming 15 Ω/cm$^2$ (1,200 Å) ITO. m-MTDATA was vacuum deposited on the anode to form a HIL with a thickness of 750 Å. α-NPD was vacuum deposited on the HIL to form a HTL with a thickness of 150 Å. 97 wt % of DSA as a host and 3 wt % of TBPe as a dopant were deposited on the HTL to form an EML with a thickness of 300 Å. Alq3 was vacuum deposited on the EML to form an ETL with a thickness of 200 Å. LiF was vacuum deposited on the ETL to form an EIL with a thickness of 80 Å and Al was vacuum deposited on the EIL to form a cathode with a thickness of 3000 Å.

Examples 2 to 5

OLEDs were manufactured in the same manner as in Example 1, except that Compounds 32, 33, 34 and 35 were used instead of Compound 11 as the material used to form the luminescent efficiency improvement layer.

Comparative Example

An OLED was manufactured in the same manner as in Example 1, except that Alq3 was used instead of Compound 11 as the material used to form the luminescent efficiency improvement layer.

Evaluation Example 1

Efficiency (cd/A) of the OLEDs manufactured according to Examples 1 to 5 and the OLED manufactured according to Comparative Example was measured using a PR650 (Spectroscan) Source Measurement Unit. (PhotoResearch, Inc.), and thus results are shown in Table 1 below.

TABLE 1

| | Compound in luminescent efficiency improvement layer | Efficiency (cd/A) |
|---|---|---|
| Example 1 | Compound 11 | 3.6 |
| Example 2 | Compound 32 | 3.8 |
| Example 3 | Compound 33 | 3.6 |
| Example 4 | Compound 34 | 3.6 |
| Example 5 | Compound 35 | 3.6 |
| Comparative Example | Alq3 | 3.1 |

The OLED including the luminescent efficiency improvement layer containing the compound represented by Formula 1 can have excellent luminescent efficiency.

While the present invention has been particularly shown and described with reference to exemplary embodiments thereof, it will be understood by those of ordinary skill in thert that various changes in form and details may be made therein without departing from the spirit and scope of the present invention as defined by the following claims.

What is claimed is:
1. An organic light emitting diode (OLED) comprising:
a substrate;
a first electrode formed on the substrate, the first electrode having a second surface facing the substrate and a first surface opposite to the substrate;
an organic layer formed on the first electrode, the organic layer facing the first surface of the first electrode;
a second electrode formed on the organic layer, the second electrode having a first surface facing the organic layer and a second surface opposite to the organic layer; and
a luminescent efficiency improvement layer formed on at least one of the second surface of the second electrode and the second surface of the first electrode, the luminescent efficiency improvement layer comprising a compound represented by Formula 1:

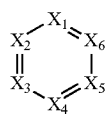
(1)

wherein $X_1$ is N or a group represented by $C-(Ar_1)_a-R_1$;

$X_2$ is N or a group represented by $C-(Ar_2)_b-R_2$;

$X_3$ is N or a group represented by $C-(Ar_3)_c-R_3$;

$X_4$ is N or a group represented by $C-(Ar_4)_d-R_4$;

$X_5$ is N or a group represented by $C-(Ar_5)_e-R_5$;

$X_6$ is N or a group represented by $C-(Ar_6)_f-R_6$, with the proviso that at least one of $X_1$ to $X_6$ is N;

$Ar_1$ to $Ar_6$ are each independently a substituted or unsubstituted $C_6$-$C_{30}$ arylene group or a substituted or unsubstituted $C_2$-$C_{30}$ heteroarylene group;

$R_1$ to $R_6$ are each independently a hydrogen atom, a halogen atom, a hydroxyl group, a cyano group, a substituted or unsubstituted $C_1$-$C_{30}$ alkyl group, a substituted or unsubstituted $C_1$-$C_{30}$ alkoxy group, a substituted or unsubstituted $C_1$-$C_{30}$ acyl group, a substituted or unsubstituted $C_2$-$C_{30}$ alkynyl group, a substituted or unsubstituted $C_6$-$C_3$ aryl group, or an unsubstituted $C_2$-$C_{30}$ heteroaryl group, wherein at least two adjacent groups of $R_1$ to $R_6$ are optionally bonded to each other to form a saturated or unsaturated ring, a substituent of the substituted $C_6$-$C_{30}$ aryl group is a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{30}$ alkyl group, a $C_1$-$C_{30}$ alkenyl group, a $C_1$-$C_{30}$ alkynyl group, a $C_6$-$C_{30}$ aryl group, a $C_7$-$C_{20}$ arylalkyl group or a $C_3$-$C_{30}$ heteroarylalkyl group; and a, b, c, d, e and f are each independently an integer of 0 to 10.

2. The OLED of claim 1, wherein $X_1$, $X_3$ and $X_5$ are N, and $X_2$, $X_4$ and $X_6$ are not N.

3. The OLED of claim 1, wherein $X_1$, $X_3$ and $X_4$ are N, and $X_2$, $X_5$ and $X_6$ are not N.

4. The OLED of claim 1, wherein $X_1$ and $X_3$ are N, and X), $X_4$, $X_5$ and $X_6$ are not N.

5. The OLED of claim 1, wherein $X_1$ and $X_4$ are N, and $X_2$, $X_3$, $X_5$ and $X_6$ are not N.

6. The OLED of claim 1, wherein $X_1$ is N, and $X_2$ to $X_6$ are not N.

7. The OLED of claim 1, wherein the compound of Formula 1 is one of the compounds represented by Formulae 1a to 1e below:

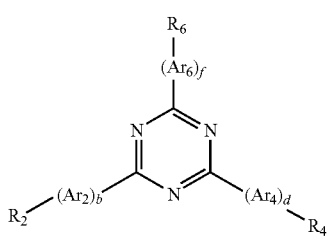
(1a)

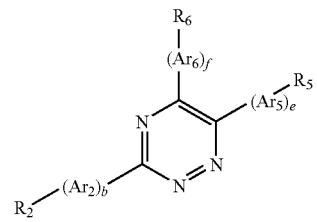
(1b)

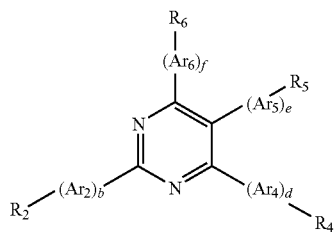
(1c)

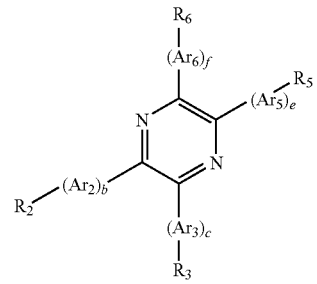
(1d)

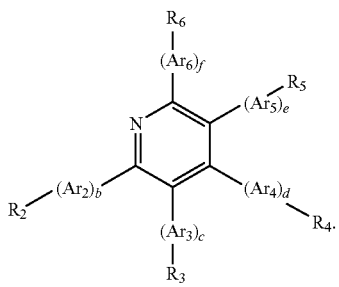
(1e)

8. The OLED of claim 1, wherein $Ar_1$ to $Ar_6$ are each independently selected from the group consisting of a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylenylene group, a substituted or unsubstituted fluorenylene group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted benzofuranylene group, a substituted or unsubstituted thiophenylenylene group, a substituted or unsubstituted benzothiophenylene group, a substituted or unsubstituted isothiazolylene group, a substituted or unsubstituted isoxazolylene group, and a substituted or unsubstituted triazolylene group.

9. The OLED of claim 1, wherein $Ar_1$ to $Ar_6$ are each independently one of the groups represented by Formulae 2a to 2p below:

Formula 2a

Formula 2b
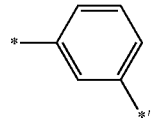

Formula 2c
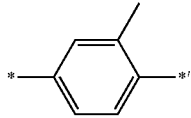

Formula 2d
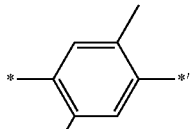

Formula 2e
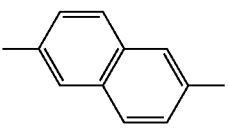

Formula 2f
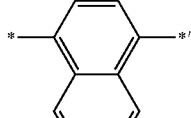

Formula 2g
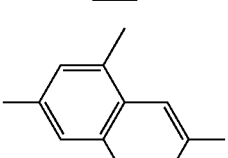

Formula 2h
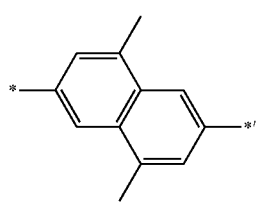

Formula 2i
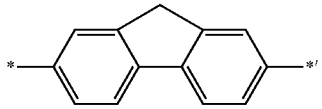

Formula 2j
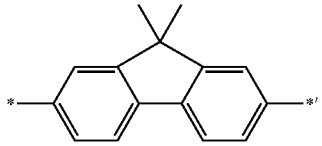

Formula 2k
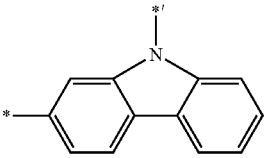

Formula 2l
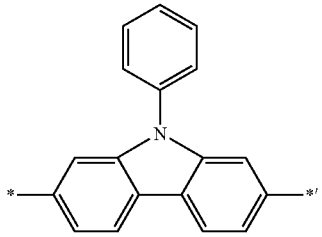

Formula 2m
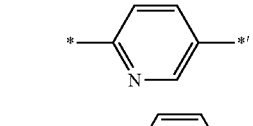

Formula 2n
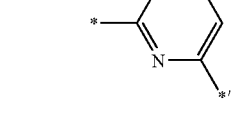

Formula 2o
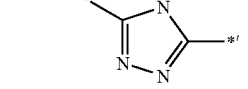

Formula 2p
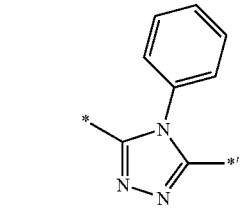

wherein * indicates a site bound to C which is a cyclic element of a 6-membered aromatic ring shown in Formula 1, and *' indicates a site bound to one of $R_1$ to $R_6$.

10. The OLED of claim 1, wherein $R_1$ to $R_6$ are each independently selected from the group consisting of a hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_1$-$C_{10}$ acyl group, a substituted or unsubstituted $C_2$-$C_{10}$ alkenyl group, a substituted or unsubstituted $C_2$-$C_{10}$ alkynyl group, a substituted or unsubstituted $C_6$-$C_{14}$ aryl group, and an unsubstituted $C_2$-$C_{14}$ heteroaryl group, and a substituent of the substituted $C_6$-$C_{14}$ aryl group is a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{30}$ alkyl group, a $C_1$-$C_{30}$ alkenyl group, a $C_1$-$C_{30}$ alkynyl group, a $C_6$-$C_{30}$ aryl group, a $C_7$-$C_{20}$ arylalkyl group or a $C_3$-$C_{30}$ heteroarylalkyl group.

11. The OLED of claim 1, wherein $R_1$ to $R_6$ are each independently one of the groups represented by Formulae 3a to 3h and 3j to 3q below:

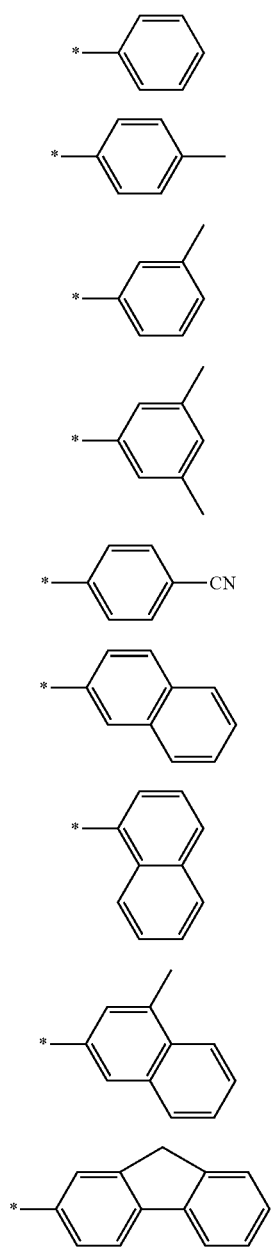

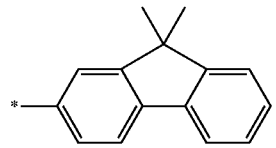

Formula 3k

Formula 3l

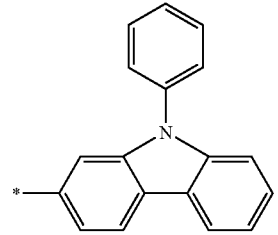

Formula 3m

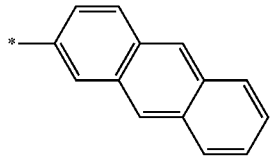

Formula 3n

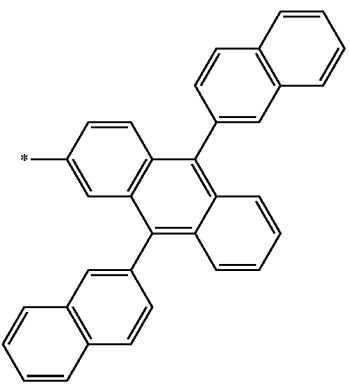

Formula 3o

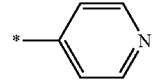

Formula 3p

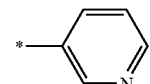

Formula 3q

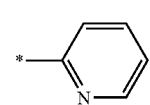

wherein * indicates a site bound to C which is a cyclic element of a 6-membered aromatic ring shown in Formula 1, or a site bound to one of $Ar_1$ to $Ar_6$.

12. The OLED of claim 1, wherein the group represented by —$(Ar_1)_a$—$R_1$, the group represented by —$(Ar_2)_b$—$R_2$, the group represented by —$(Ar_3)_c$—$R_3$, the group represented by —$(Ar_4)_d$—$R_4$, the group represented by —$(Ar_5)_e$—$R_5$, and the group represented by —$(Ar_6)_f$—$R_6$ are each independently one of the groups represented by Formulae 4a to 4y below:

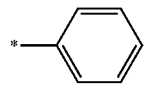

Formula 4a

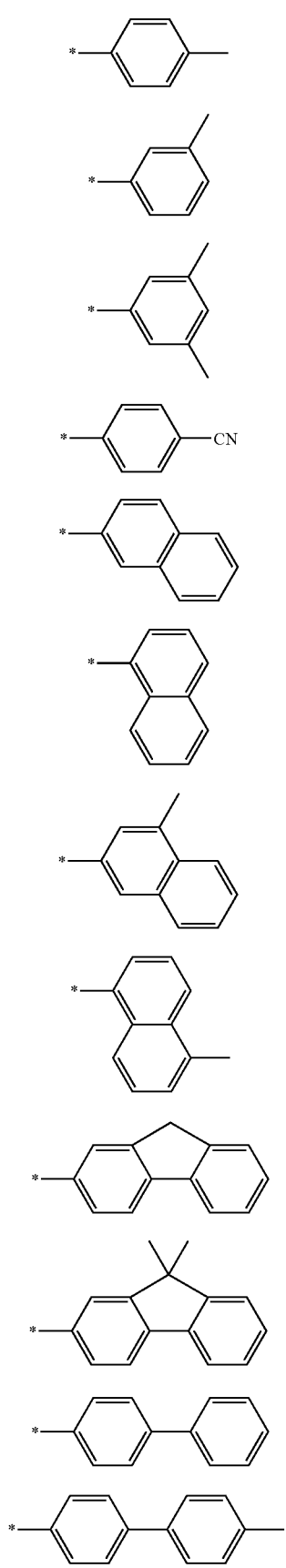
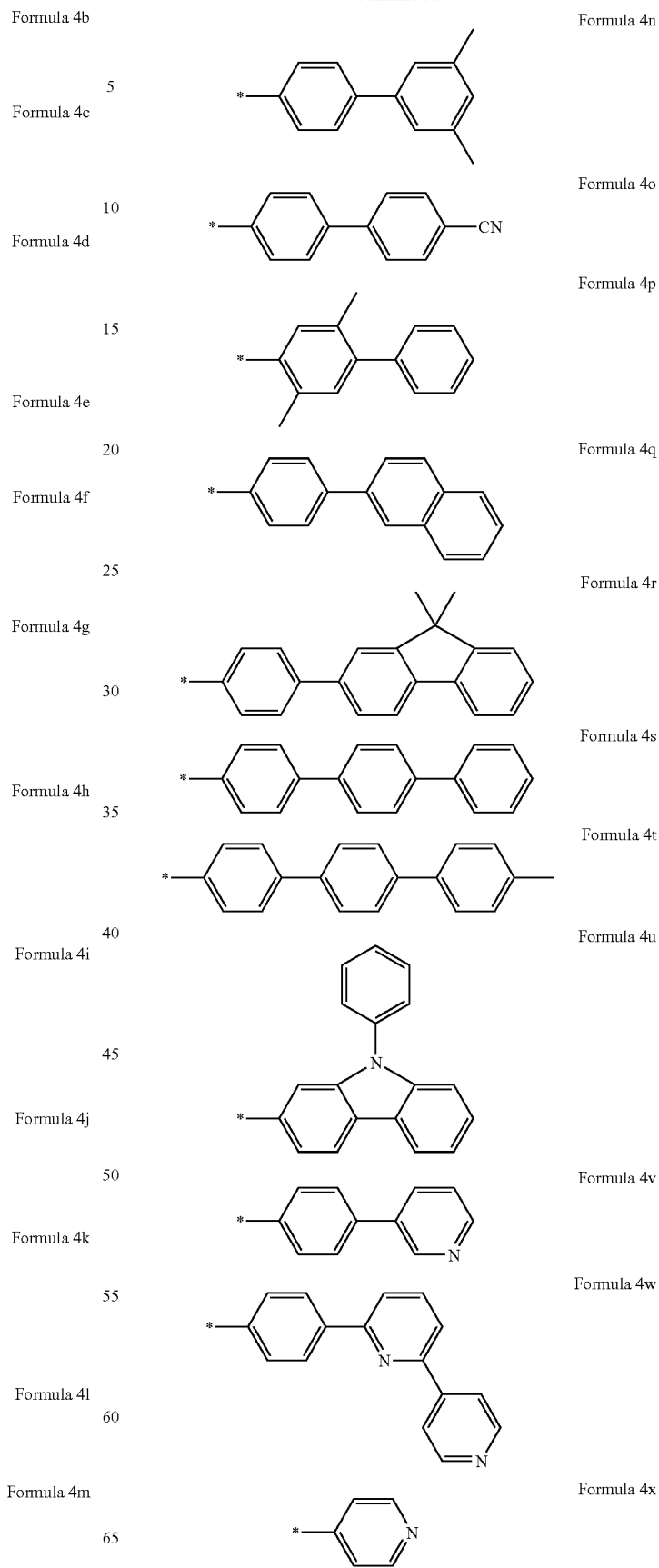

Formula 4y
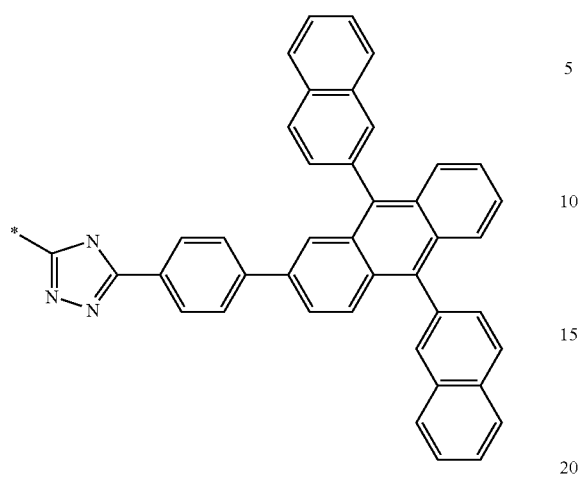
wherein * indicates a site bound to C which is a cyclic element of a 6-membered aromatic ring shown in Formula 1.
13. The OLED of claim 1, wherein the compound represented by Formula 1 is one selected from the group consisting of Formulae 5 through 39:
(5)
[Formula 5 structure]
(6)
[Formula 6 structure]
(7)
[Formula 7 structure]
(8)
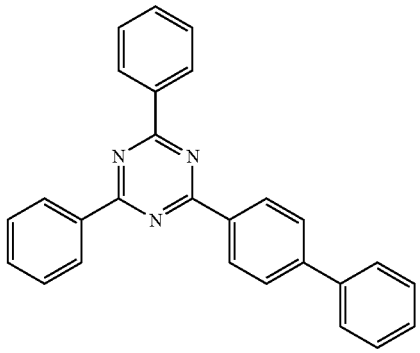
(9)
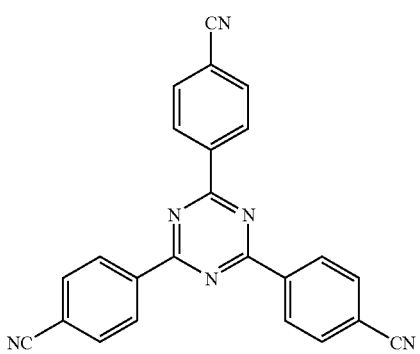
(10)
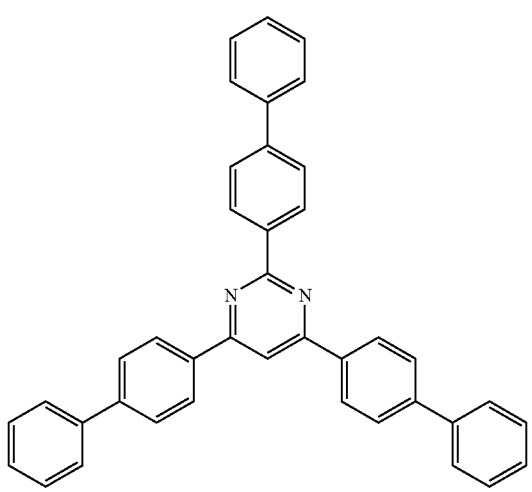
(11)
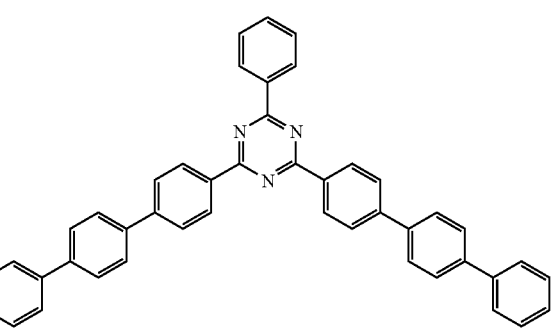

(12)
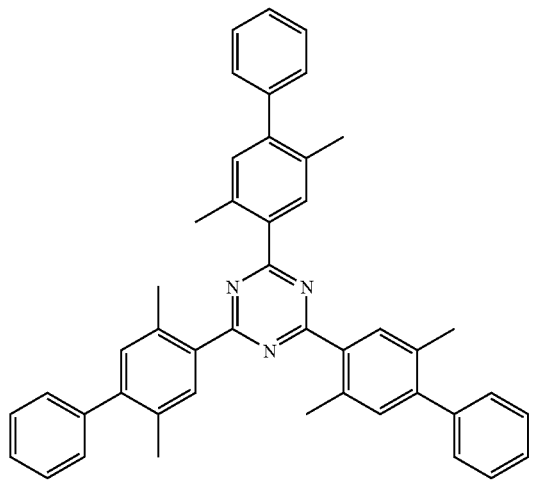
(13)
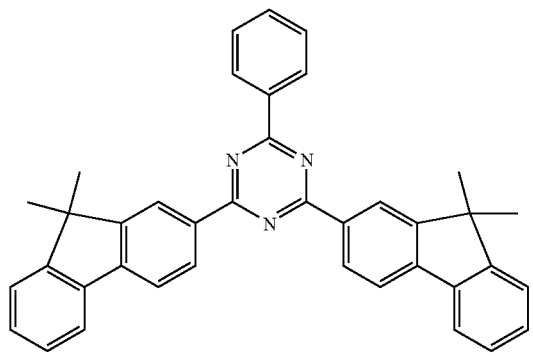
(14)
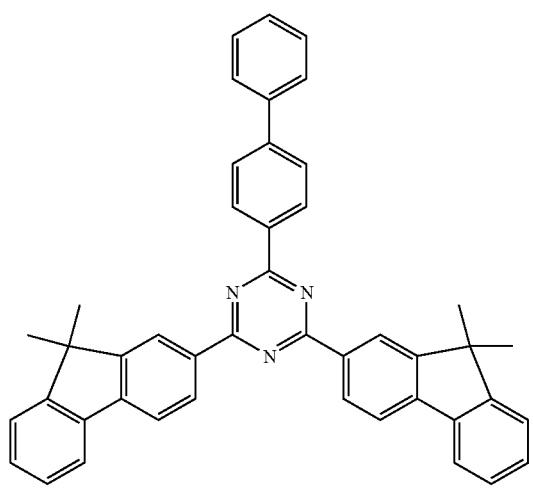
(15)
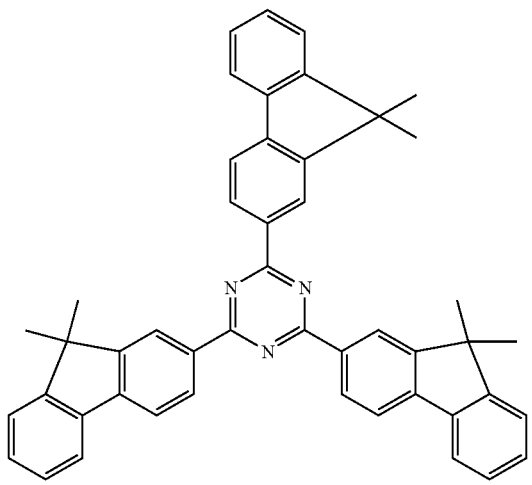
(16)
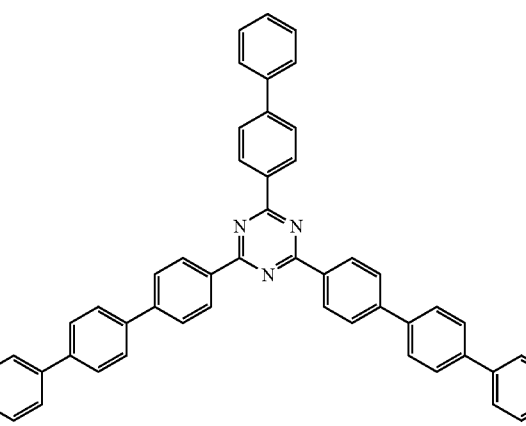
(17)
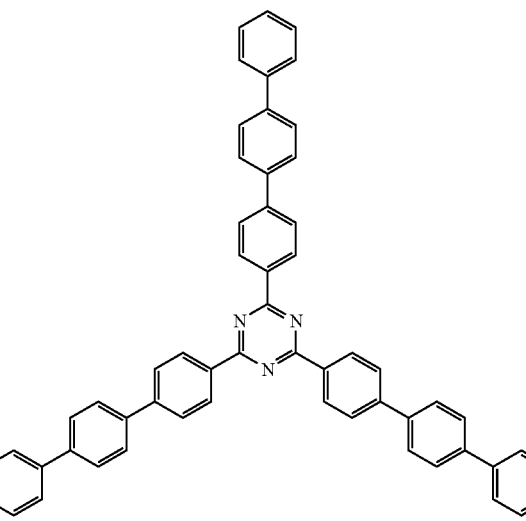

-continued
(18)
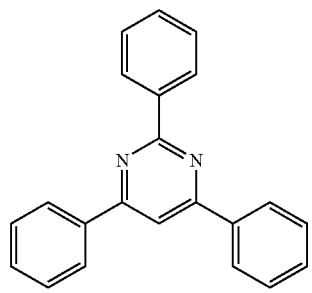
(19)
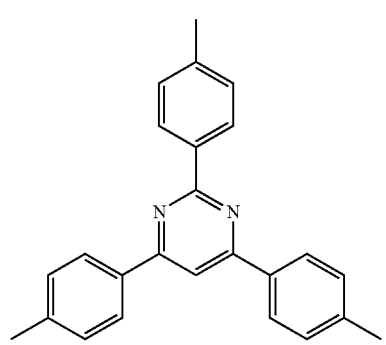
(20)
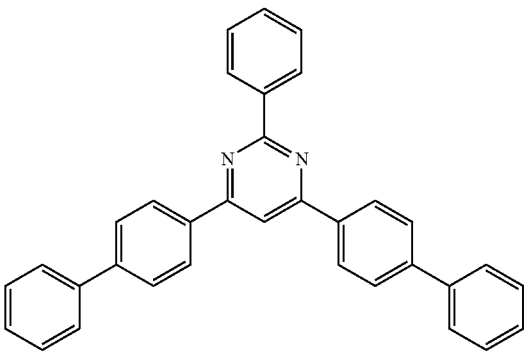
(21)
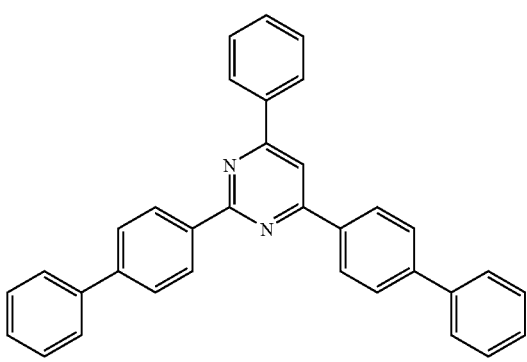
(22)
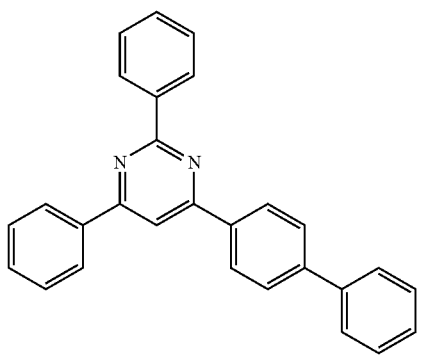
(23)
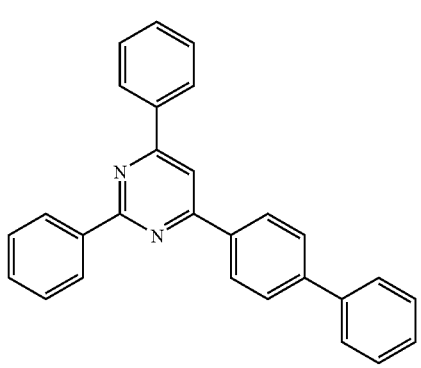
(24)
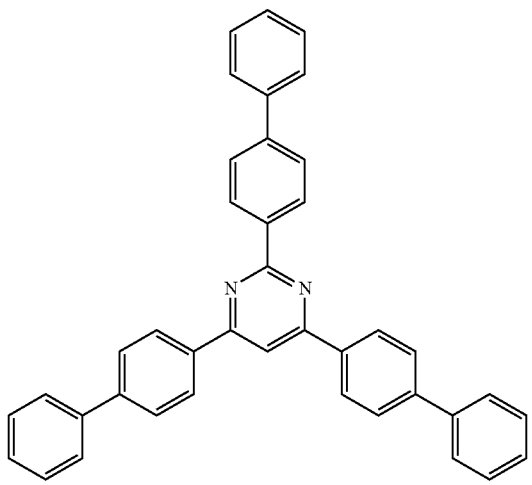
(25)

(26)
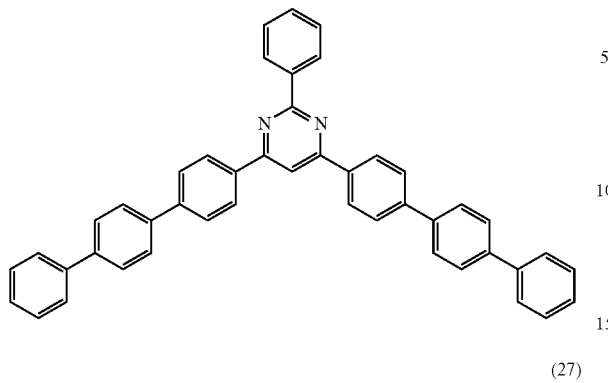
(27)
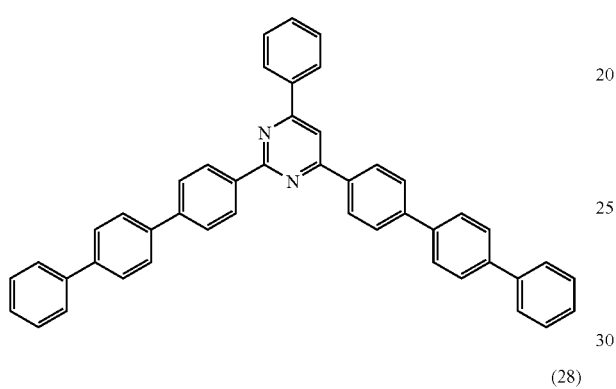
(28)
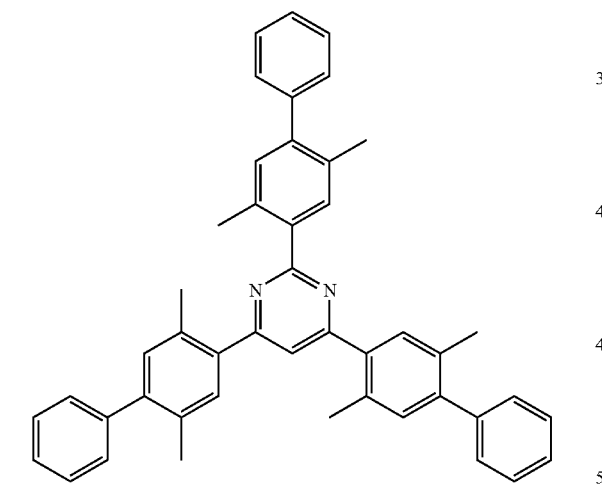
(29)
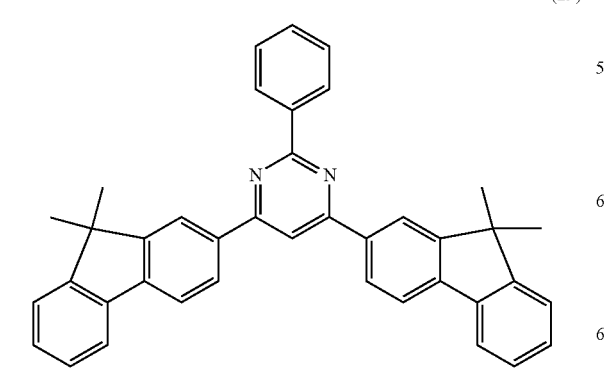
(30)
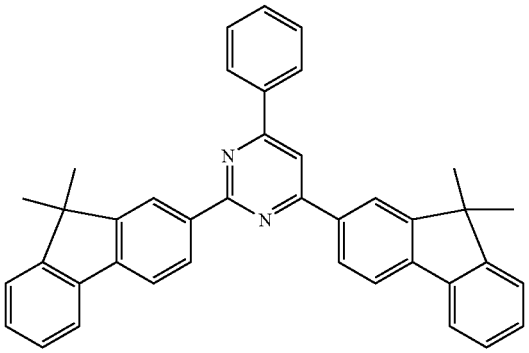
(31)
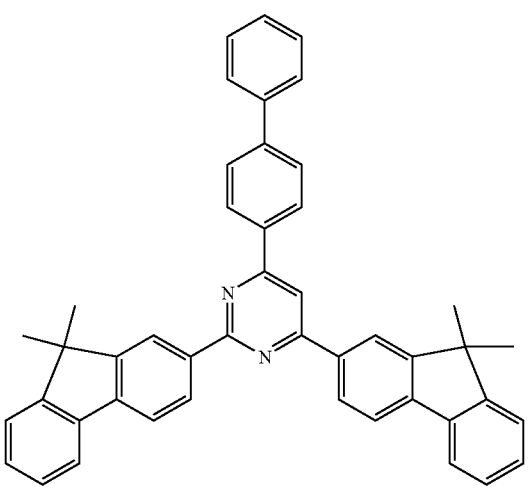
(32)

(33)
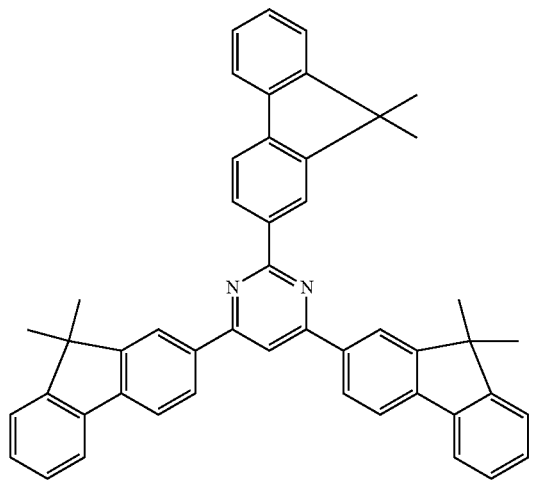
(36)
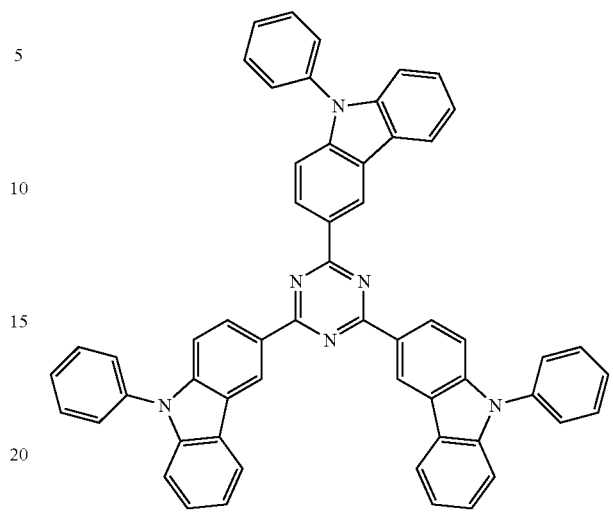
(34)
(37)
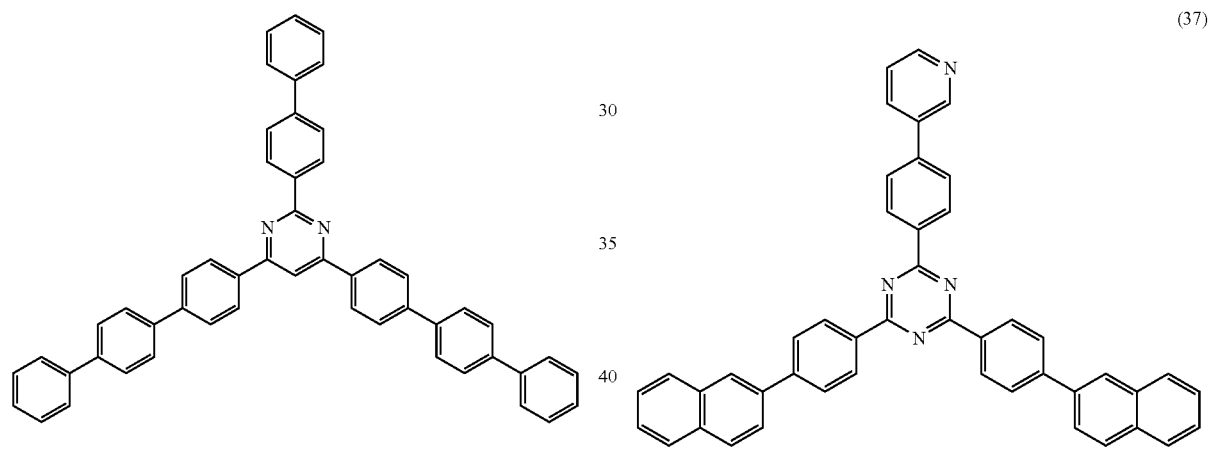
(35)
(38)
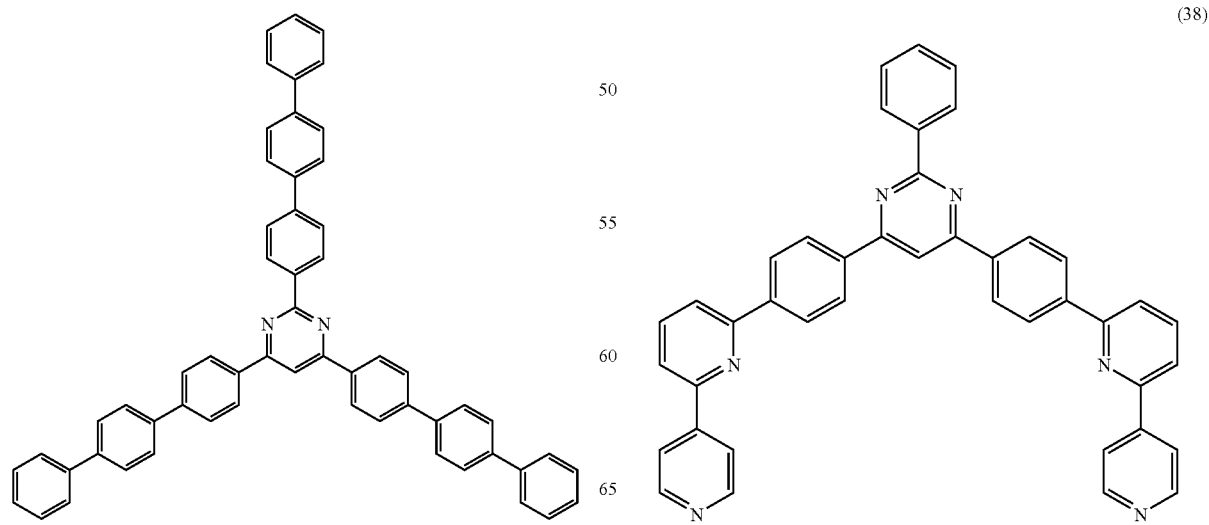

-continued (39)

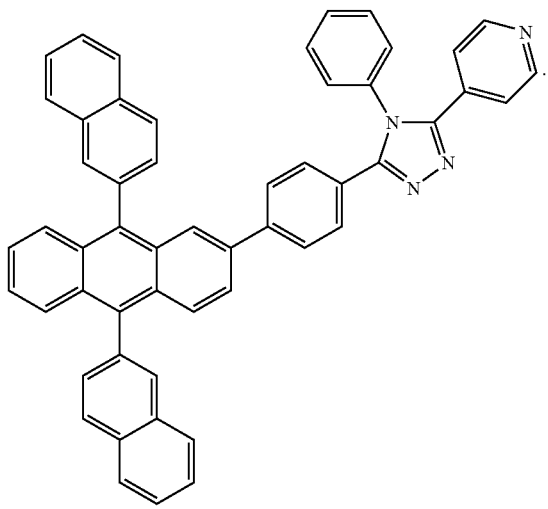

14. The OLED of claim 1, wherein the second electrode is a transmission electrode, and the luminescent efficiency improvement layer is formed on the second surface of the second electrode.

15. The OLED of claim 1, wherein the first electrode is a transmission electrode, and the luminescent efficiency improvement layer is formed on the second surface of the first electrode.

16. The OLED of claim 1, wherein the first electrode and the second electrode are transmission electrodes, and the luminescent efficiency improvement layer is formed on the second surface of the second electrode and on the second surface of the first electrode.

17. The OLED of claim 1, wherein the luminescent efficiency improvement layer comprises a luminescent efficiency improvement layer -R, a luminescent efficiency improvement layer -G, and a luminescent efficiency improvement layer -B.

18. An organic light emitting diode (OLED) comprising:
a substrate;
a first electrode formed on the substrate,
a second electrode having a first surface facing the first electrode and a second surface opposite to the first surface;
an organic layer interposed between the first electrode and the second electrode;
a first luminescent efficiency improvement layer formed on the second surface of the electrode, the first luminescent efficiency improvement layer comprising a compound represented by Formula 1:

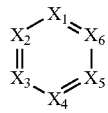

(1)

wherein $X_1$ is N or a group represented by C—$(Ar_1)_a$—$R_1$;
$X_2$ is N or a group represented by C—$(Ar_2)_b$—$R_2$;
$X_3$ is N or a group represented by C—$(Ar_3)_c$—$R_3$;
$X_4$ is N or a group represented by C—$(Ar_4)_d$—$R_4$;
$X_5$ is N or a group represented by C—$(Ar_5)_e$—$R_5$;
$X_6$ is N or a group represented by C—$(Ar_6)_f$—$R_6$, with the proviso that at least one of $X_1$ to $X_6$ is N;
$Ar_1$ to $Ar_6$ are each independently a substituted or unsubstituted $C_6$-$C_{10}$ arylene group or a substituted or unsubstituted $C_2$-$C_{30}$ heteroarylene group;
$R_1$ to $R_6$ are each independently a hydrogen atom, a halogen atom, a hydroxyl group, a cyano group, a substituted or unsubstituted $C_1$-$C_{30}$ alkyl group, a substituted or unsubstituted $C_1$-$C_{30}$ alkoxy group, a substituted or unsubstituted $C_1$-$C_{30}$ acyl group, a substituted or unsubstituted $C_2$-$C_{30}$ alkynyl group, a substituted or unsubstituted $C_6$-$C_{30}$ aryl group, or an unsubstituted $C_2$-$C_{30}$ heteroaryl group, wherein at least two adjacent groups of $R_1$ to $R_6$ are optionally bonded to each other to form a saturated or unsaturated ring, and a substituent of the substituted $C_6$-$C_{30}$ aryl group is a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{30}$ alkyl group, a $C_1$-$C_{30}$ alkenyl group, a $C_1$-$C_{30}$ alkynyl group, a $C_6$-$C_{30}$ aryl group, a $C_7$-$C_{20}$ arylalkyl group or a $C_3$-$C_{30}$ heteroarylalkyl group; and
a, b, c, d, e and f are each independently an integer of 0 to 10; and
optionally at least one additional layer formed between the second electrode and the first luminescent efficiency improvement layer.

19. An organic light emitting diode (OLED) of claim 18, further comprising a second luminescent efficiency improvement layer formed between the substrate and the first electrode.

20. An organic light emitting diode (OLED) comprising:
a substrate;
a first electrode formed on the substrate,
a second electrode having a first surface facing the first electrode and a second surface opposite to the first surface;
an organic layer interposed between the first electrode and the second electrode;
a luminescent efficiency improvement layer formed between the substrate and the first electrode, the luminescent efficiency improvement layer comprising a compound represented by Formula 1:

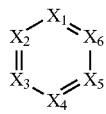

(1)

wherein $X_1$ is N or a group represented by C—$(Ar_1)_a$—$R_1$;
$X_2$ is N or a group represented by C—$(Ar_2)_b$—$R_2$;
$X_3$ is N or a group represented by C—$(Ar_3)_c$—$R_3$;
$X_4$ is N or a group represented by C—$(Ar_4)_d$—$R_4$;
$X_5$ is N or a group represented by C—$(Ar_5)_e$—$R_5$;
$X_6$ is N or a group represented by C—$(Ar_6)_f$—$R_6$, with the proviso that at least one of $X_1$ to $X_6$ is N;
$Ar_1$ to $Ar_6$ are each independently a substituted or unsubstituted $C_6$-$C_{30}$ arylene group or a substituted or unsubstituted $C_2$-$C_{30}$ heteroarylene group;

$R_1$ to $R_6$ are each independently a hydrogen atom, a halogen atom, a hydroxyl group, a cyano group, a substituted or unsubstituted $C_1$-$C_{30}$ alkyl group, a substituted or unsubstituted $C_1$-$C_{30}$ alkoxy group, a substituted or unsubstituted, $C_1$-$C_{30}$ acyl group, a substituted or unsubstituted $C_2$-$C_{30}$ alkynyl group, a substituted or unsubstituted $C_6$-$C_{30}$ aryl group, or an unsubstituted $C_2$-$C_{30}$ heteroaryl group, wherein at least two adjacent groups of $R_1$ to $R_6$ are optionally bonded to each other to form a saturated or unsaturated ring, and a substituent of the substituted $C_6$-$C_{30}$ aryl group is a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{30}$ alkyl group, a $C_1$-$C_{30}$ alkenyl group, a $C_1$-$C_{30}$ alkynyl group, a $C_6$-$C_{30}$ aryl group, a $C_7$-$C_{20}$ arylalkyl group or a $C_3$-$C_{30}$ heteroarylalkyl group; and a, b, c, d, e and f are each independently an integer of 0 to 10; and optionally at least one additional layer formed between the first electrode and the luminescent efficiency improvement layer.

21. The OLED of claim 20, wherein $R_1$ to $R_6$ are each independently a halogen atom, a hydroxyl group, a cyano group, a substituted or unsubstituted $C_1$-$C_{30}$ alkoxy group, a substituted or unsubstituted $C_2$-$C_{30}$ alkynyl group, a substituted or unsubstituted $C_6$-$C_{30}$ aryl group, or an unsubstituted $C_2$-$C_{30}$ heteroaryl group, wherein at least two adjacent groups of $R_1$ to $R_6$ are optionally bonded to each other to form a saturated or unsaturated ring, and a substituent of the substituted $C_6$-$C_{30}$ aryl group is a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{30}$ alkyl group, a $C_1$-$C_{30}$ alkenyl group, a $C_1$-$C_{30}$ alkynyl group, a $C_6$-$C_{30}$ aryl group, a $C_7$-$C_{20}$ arylalkyl group or a $C_3$-$C_{30}$ heteroarylalkyl group.

22. The OLED of claim 1, wherein the compound of Formula 1 is a compound represented by Formula 1a below:

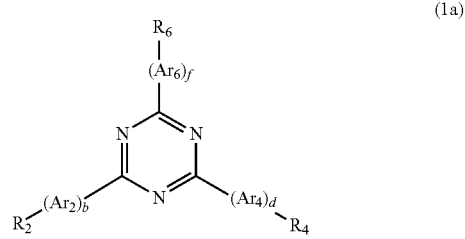

(1a)

wherein $Ar_2$, $Ar_4$ and $Ar_6$ are a substituted or unsubstituted $C_2$-$C_{30}$ heteroarylene group;

b, d and f are 1; and $R_2$, $R_4$ and $R_6$ are a substituted or unsubstituted $C_6$-$C_{30}$ aryl group.

* * * * *